(12) United States Patent
Synder et al.

(10) Patent No.: US 7,326,253 B2
(45) Date of Patent: Feb. 5, 2008

(54) PROSTHETIC CUP ASSEMBLY HAVING INCREASED ASSEMBLY CONGRUENCY

(75) Inventors: Duane G. Synder, Scottsdale, AZ (US); Leanne A. Turner, North Webster, IN (US); James G. Lancaster, Warsaw, IN (US); Paul P. Lewis, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 78 days.

(21) Appl. No.: 10/278,577

(22) Filed: Oct. 23, 2002

(65) Prior Publication Data

US 2003/0105529 A1    Jun. 5, 2003

Related U.S. Application Data

(60) Provisional application No. 60/333,180, filed on Nov. 16, 2001.

(51) Int. Cl.
*A61F 2/32* (2006.01)
(52) U.S. Cl. ..................................... 623/22.4
(58) Field of Classification Search ............. 623/11.11, 623/16.11, 18.11, 22.11, 22.15, 22.17, 22.19, 623/22.2, 22.21, 22.24, 22.25, 22.28, 22.29, 623/22.32, 23.34
See application file for complete search history.

(56) References Cited

U.S. PATENT DOCUMENTS

| | | |
|---|---|---|
| 2,910,978 A | 11/1959 | Urist |
| 3,584,318 A | 6/1971 | Scales et al. |
| 3,744,061 A | 7/1973 | Frost |
| 3,806,960 A | 4/1974 | Weber |
| 3,829,904 A | 8/1974 | Ling et al. |
| 4,031,570 A | 6/1977 | Frey |
| 4,596,580 A | 6/1986 | Weill |

(Continued)

FOREIGN PATENT DOCUMENTS

DE    196 16 059 A1    10/1997

(Continued)

OTHER PUBLICATIONS

H. Henning Freden, "Tapers, Spindle Noses, and Arbors", *Tool Engineer's Handbook*, pp. 1848-1860.
P.A. Dearnley, "A Review of Metallic, Ceramic and Surface-Treated Metals Used for Bearing Surfaces in Human Joint Replacements", Proc. Instn. Mech. Engrs., vol. 213, Part H, pp. 107-135.

*Primary Examiner*—Anuradha Ramana
(74) *Attorney, Agent, or Firm*—Maginot, Moore & Beck

(57) ABSTRACT

A prosthetic component assembly, such as an acetabular cup, includes a shell and a bearing insert or liner. The shell and bearing insert are configured to provide an increased congruency between the shell and the bearing insert thereby decreasing the amount of motion (i.e. micromotion) between the shell and the bearing insert. In one form, increased congruency is achieved through first and second (inner and outer) tapers that are respectively provided on the shell and the bearing insert. The outer taper has first and second outer taper portions. A relationship between the first outer taper portion and the inner provides an essentially congruent fit, while a relationship between the second taper portion and the inner taper provides an interference fit. The relationships between the inner and outer tapers allow the bearing insert to achieve load sharing at a dome of the outer shell as well as at a rim of the shell. The relationships between the tapers also allow relative motion between the shell and the bearing insert to be controlled. Particularly, the relationships between the tapers allow relative motion, or micro-motion, to be uniformly controlled below previous levels reported in the range of 10 micrometers or less between the bearing insert and the shell.

23 Claims, 30 Drawing Sheets

U.S. PATENT DOCUMENTS

| | | | |
|---|---|---|---|
| 4,650,491 | A | 3/1987 | Parchinski |
| 4,678,472 | A | 7/1987 | Noiles |
| 4,681,589 | A | 7/1987 | Tronzo |
| 4,695,282 | A | 9/1987 | Forte et al. |
| 4,704,127 | A | 11/1987 | Averill et al. |
| 4,718,911 | A | 1/1988 | Kenna |
| 4,784,663 | A | 11/1988 | Kenna |
| 4,795,470 | A | 1/1989 | Goymann et al. |
| 4,883,491 | A | 11/1989 | Mallory et al. |
| 4,892,549 | A | 1/1990 | Figgie, III et al. |
| 4,917,530 | A | 4/1990 | Engelhardt |
| 4,919,674 | A * | 4/1990 | Schelhas ............... 623/22.29 |
| 4,936,861 | A | 6/1990 | Muller et al. |
| 4,978,356 | A | 12/1990 | Noiles |
| 5,002,577 | A | 3/1991 | Bolesky et al. |
| 5,019,105 | A | 5/1991 | Wiley |
| 5,049,158 | A | 9/1991 | Engelhardt et al. |
| 5,080,677 | A | 1/1992 | Shelley |
| 5,108,445 | A | 4/1992 | Ashby |
| 5,171,285 | A | 12/1992 | Broderick |
| 5,222,984 | A | 6/1993 | Forte |
| 5,226,917 | A | 7/1993 | Schryver |
| 5,263,988 | A * | 11/1993 | Huebner ............... 623/22.29 |
| 5,282,864 | A | 2/1994 | Noiles et al. |
| 5,310,408 | A | 5/1994 | Schryver et al. |
| 5,358,532 | A | 10/1994 | Evans et al. |
| 5,383,938 | A | 1/1995 | Rohr et al. |
| 5,413,603 | A | 5/1995 | Noiles et al. |
| 5,413,610 | A | 5/1995 | Amino |
| 5,443,519 | A | 8/1995 | Averill et al. |
| 5,507,824 | A | 4/1996 | Lennox |
| 5,549,698 | A | 8/1996 | Averill et al. |
| 5,571,198 | A | 11/1996 | Drucker et al. |
| 5,571,201 | A | 11/1996 | Averill et al. |
| 5,577,368 | A | 11/1996 | Hamilton et al. |
| 5,641,323 | A | 6/1997 | Caldarise |
| 5,645,601 | A | 7/1997 | Pope et al. |
| 5,645,606 | A | 7/1997 | Oehy et al. |
| 5,658,294 | A | 8/1997 | Sederholm |
| 5,658,346 | A | 8/1997 | Willi |
| 5,658,347 | A | 8/1997 | Sarkisian et al. |
| 5,658,348 | A | 8/1997 | Rohr, Jr. |
| 5,676,704 | A | 10/1997 | Ries et al. |
| 5,702,456 | A | 12/1997 | Pienkowski |
| 5,702,476 | A | 12/1997 | Limacher et al. |
| 5,702,477 | A | 12/1997 | Capello et al. |
| 5,702,478 | A | 12/1997 | Tornier |
| 5,702,483 | A | 12/1997 | Kwong |
| 5,711,973 | A | 1/1998 | Rothschild et al. |
| 5,725,589 | A | 3/1998 | Pfaff et al. |
| 5,755,803 | A | 5/1998 | Haines et al. |
| 5,755,808 | A | 5/1998 | DeCarlo et al. |
| 5,756,027 | A | 5/1998 | Rothschild et al. |
| 5,782,928 | A | 7/1998 | Ries et al. |
| 5,782,929 | A | 7/1998 | Sederholm |
| 5,782,930 | A | 7/1998 | Lin et al. |
| 5,788,916 | A | 8/1998 | Caldaries |
| 5,871,547 | A | 2/1999 | Abouaf et al. |
| 5,879,397 | A * | 3/1999 | Kalberer et al. ......... 623/22.25 |
| 5,879,402 | A | 3/1999 | Lawes et al. |
| 5,879,404 | A | 3/1999 | Bateman et al. |
| 5,879,405 | A | 3/1999 | Ries et al. |
| 5,879,406 | A | 3/1999 | Lilley |
| 5,879,407 | A | 3/1999 | Waggener |
| 5,888,204 | A | 3/1999 | Ralph et al. |
| 5,888,205 | A | 3/1999 | Pratt et al. |
| 5,935,175 | A | 8/1999 | Ostiguy, Jr. et al. |
| 5,938,701 | A * | 8/1999 | Hiernard et al. ............ 606/99 |
| 6,129,765 | A | 10/2000 | Lopez et al. |
| 6,132,469 | A * | 10/2000 | Schroeder ............... 623/22.24 |
| 6,152,961 | A * | 11/2000 | Ostiguy et al. .......... 623/22.28 |
| 6,368,354 | B2 * | 4/2002 | Burstein et al. ......... 623/22.28 |
| 6,527,808 | B1 * | 3/2003 | Albertorio et al. ....... 623/22.26 |
| 6,682,566 | B2 * | 1/2004 | Draenert ............... 623/22.24 |

FOREIGN PATENT DOCUMENTS

| | | |
|---|---|---|
| DE | 19654409 | 4/1998 |
| EP | 0 137 664 A2 | 8/1984 |
| EP | 0 214 885 A1 | 7/1986 |
| EP | 0 302 850 B1 | 7/1988 |
| EP | 0 315 795 A1 | 10/1988 |
| EP | 0349450 | 1/1990 |
| EP | 0389392 | 9/1990 |
| EP | 0444381 | 9/1991 |
| EP | 0 648 478 A2 | 4/1995 |
| EP | 0 773 007 A1 | 5/1997 |
| EP | 0826347 | 3/1998 |
| EP | 0958797 | 11/1999 |
| EP | 1133958 | 9/2001 |
| FR | 2793137 A1 * | 11/2000 |
| WO | WO88/07356 | 10/1988 |
| WO | WO 95/22944 | 8/1995 |
| WO | WO 95/23566 | 9/1995 |
| WO | WO 96/04862 | 2/1996 |
| WO | WO 96/04866 | 2/1996 |
| WO | WO 96/04867 | 2/1996 |
| WO | WO 96/23457 | 8/1996 |
| WO | WO96/25128 | 8/1996 |
| WO | WO 97/16138 | 5/1997 |

* cited by examiner

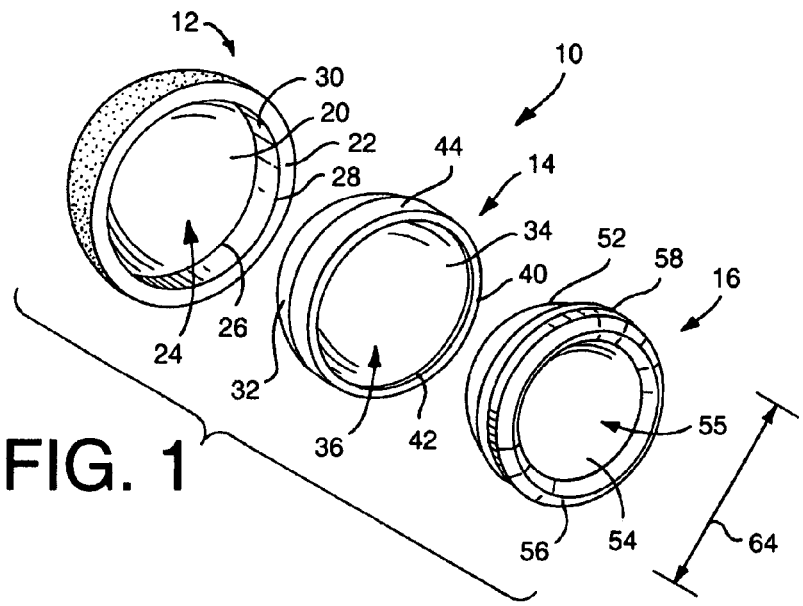
FIG. 1
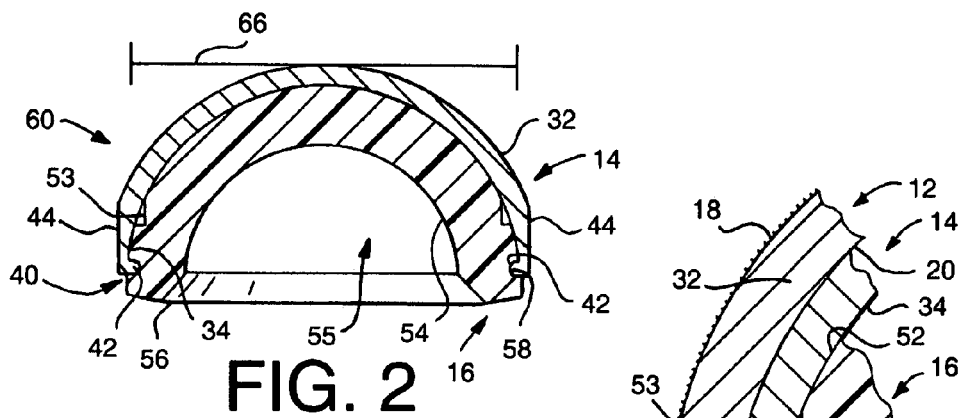
FIG. 2
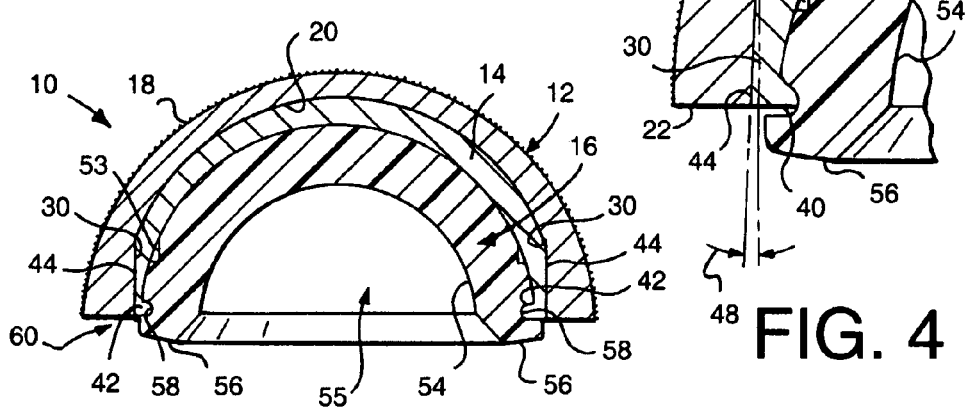
FIG. 3
FIG. 4

PROSTHETIC CUP ASSEMBLY HAVING INCREASED ASSEMBLY CONGRUENCY

This application claims the benefit of U.S. Provisional Application Ser. No. 60/333,180, filed Nov. 16, 2001.

BACKGROUND

1. Field of the Invention

The present invention is directed to a prosthetic cup assembly that is disclosed in the context of a hip prosthesis.

2. Background Information

It is known to provide an acetabular cup assembly that includes a metal shell component for attachment to an acetabulum to replace the natural socket and a plastic bearing component that is inserted into the shell to provide a bearing surface for receiving a femur ball prosthesis element. See for example, U.S. Pat. No. 5,049,158, to John A. Englehardt et al., the disclosure of which is expressly incorporated herein by reference. In addition, traditional bearing components include a built-up lip around a portion of the bearing surface. See for example, U.S. Pat. Nos. 5,288,864 and 5,413,603 to Noiles et al., the disclosures of which are also expressly incorporated herein by reference.

A problem that can occur with such acetabular cup assemblies is motion between the outer metal shell and the plastic bearing component or insect. Motion between the outer metal shell and the plastic bearing insert causes wear and thus the possibility of wear debris particles. Wear debris particles have been associated with particle-induced osteolysis. In view of this, it is desirable to reduce or eliminate motion between the metal shell and the plastic insert of acetabular cup assemblies.

Previous acetabular cup assembly designs have focused on macroscopic motion between the metal shell and the plastic insert. Other designs have sought to decrease the amount of particles generated by such motion by decreasing the surface finish at the surface of interaction between the metal shell and the plastic insert (see U.S. Pat. No. 5,310,408 issued to Schryver et al.). Still further, acetabular cup assembly designs have focused on using a third member as a way to maintain macrostability of the assembly parts while maintaining dome loading. Dome loading designs essentially ensure contact in the dome region by leaving clearance under the lip of the liner. These dome loading designs however, cause the insert to seat in the direction of the applied load.

Referring to FIGS. 20 and 21, there is shown a prior acetabular cup assembly, generally designated 500. The prior acetabular cup assembly 500 represents a typical dome loading ring lock design and includes a shell 502 and a bearing insert or liner (not seen in the figures) that is disposed interior of the shell 502. The portion of the acetabular cup assembly 500 that is shaded, depicts or represents congruency between the liner and the shell 502 of the acetabular cup assembly 500 when a load is applied to the inside of the liner at 20° relative to an axis defined from the center opening 504. The shaded portion of the shell 502 may thus be considered a load pattern and is generally designated 506. Thus, the remaining portion of the shell 502 that is not shaded represents non-congruency between the liner and the shell 502.

In particular, prior dome loading ring lock designs primarily load on a spherical surface. This causes the liner (typically polyethylene) to seat against the inner surface of the shell 502 in the direction of the applied load. As the applied load shifts from one direction to another direction, the loading pattern 506 shifts about the shell. This shifting motion applied to the liner that is then in turn applied to the shell causes wear on the liner.

It is thus desirable to reduce and/or obviate the above-described condition in a prosthetic component assembly. It is further desirable to provide a prosthetic component assembly that has increased congruency between a liner and shell of the prosthetic component assembly. It is also desirable to provide a prosthetic component assembly that maintains an increased congruency between a liner and a shell thereof regardless of loading induced on the liner. It is still further desirable to provide a prosthetic component assembly that provides controllable motion between a liner and a shell of the prosthetic component assembly. It is yet further desirable to provide a prosthetic component assembly that provides uniform controllable motion between a liner and a shell thereof.

SUMMARY

According to the subject invention, a prosthetic cup assembly for use in a joint such as a hip joint is provided. The prosthetic cup assembly includes a shell defining a cavity, and a bearing insert or liner adapted for insertion into the shell cavity. The shell cavity and an outer surface of the bearing insert are configured with co-acting tapers. Use of co-acting tapers allows control of relative motion between the shell and the bearing insert.

In one form, the co-acting tapers of the shell cavity and the bearing insert outer surface provide an interference fit between the bearing insert and the shell. The tapers are positioned on the shell and bearing insert such that the bearing insert is essentially congruent with the shell.

In another form, each taper of the co-acting shell cavity taper and the bearing insert taper has a first portion and a second portion. The first and second portions are defined from a gage or transition point of the respective taper. Arbitrarily, first portions of each taper are essentially parallel and/or congruent with respect to each other, while second portions of each taper are convergent with respect to each other.

The parallel/congruent taper portions define a substantially zero interference between each other (a "negative interference"), while the convergent taper portions define non-zero interference between each other. The amount of interference between the two convergent tapers is defined by the amount of, or literally, the degree of convergence, between the two convergent taper portions. The total degree of convergence between the two convergent taper portions defines a total amount of interference between the convergent portions. The amount of interference may be varied. This is achieved by varying the angle of each convergent taper portion. Various combinations of angled convergent portions provide various interference. The interference causes the bearing insert to effectively fix with the shell. By effectively fixing the bearing insert to the shell, control of motion between the bearing insert and the shell is effectively controlled.

The length of the convergent taper portions may also be varied, including the length with respect to each other. Such variation in length of the convergent taper portions may be combined with the variation in angle of convergence of the taper portions. In this manner, the amount of interference between the shell and the bearing insert may be controlled. This translates to an amount of immobility (locking) between the bearing insert and the shell.

The subject invention effectively allows the bearing insert to substantially completely dome load with respect to the shell while also providing stability in the peripheral regions (load sharing). Since the bearing insert is fixed at both a portion of the tapers and the dome, the relative location of the bearing insert does not move or change when a load is applied to the liner.

In one form, the subject invention provides a prosthetic component assembly for use in fixation to a bone. The prosthetic component assembly includes a shell and a liner. The shell is formed with an inner surface having an inner taper. The inner taper has an inner taper angle. The liner is configured to be received in the shell and is formed with an outer surface having an outer taper. The outer taper has a first outer taper portion and a second outer taper portion. The first outer taper portion has a first outer taper angle and the second outer taper portion has a second outer taper angle. The first outer taper angle is less than or equal to the inner taper angle. The second outer taper angle is greater than the inner taper angle in a pre-assembly state of the liner.

In another form, the subject invention provides a prosthetic component assembly for use in fixation to a bone. The prosthetic component assembly includes a shell and a liner. The shell is formed with an inner surface having an inner taper. The inner taper has an inner taper angle. The liner is configured to be received in the shell and is formed with an outer surface having an outer taper. The outer taper has a first outer taper portion and a second outer taper portion. The first outer taper portion defines a first outer taper angle. The second outer taper portion defines a second outer taper angle. The first outer taper angle is less than or equal to the inner taper angle. The second outer taper angle is greater than or equal to the inner taper angle in a pre-assembly state of the liner.

In yet another form, the subject invention provides a prosthetic component assembly for use in fixation to a bone. The prosthetic component assembly includes a shell and a liner. The shell is formed with an inner surface having an inner taper. The inner taper has a first inner taper portion and a second inner taper portion. The first inner taper portion has a first inner angle, while the second inner taper portion has a second inner angle. The liner is formed with an outer surface having an outer taper. The outer taper has a first outer taper portion and a second outer taper portion. The first outer taper portion has a first outer taper angle, while the second outer taper portion has a second outer taper angle. The first outer taper angle is less than or equal to the first inner taper angle, while the second outer taper angle is greater than the second inner taper angle in a pre-assembly state of the liner.

In still another form, the subject invention is a method of assembling a prosthetic component assembly. The method includes the steps of: (a) providing a shell having a cavity with an inner surface, the inner surface having an inner taper, the inner taper having an inner taper angle; (b) providing a liner having an outer surface with an outer taper, the outer taper having a first outer taper portion and a second outer taper portion, the first outer taper portion having a first outer taper angle and the second outer taper portion having a second outer taper angle, the first outer taper angle being substantially equal to the inner taper angle, and the second outer taper angle having a pre-assembled taper angle that is greater than the inner taper angle; and (c) inserting the liner into the cavity of the shell until said second outer taper portion mechanically engages the inner taper and prevents further insertion of the liner into the cavity.

In a still further form, the subject invention is a prosthetic component assembly for use in fixation to a bone. The prosthetic component assembly includes a shell and a bearing insert. The shell has an inner surface and an inner taper disposed on the inner surface. The bearing insert has an outer surface with an outer taper disposed on the outer surface. The outer taper has a first outer taper portion and a second outer taper portion. The first outer taper portion is configured to be substantially congruent with a portion of the inner taper portion when the bearing insert is assembled into the shell, and the second outer taper portion is configured to provide an interference fit with another portion of the inner taper when the bearing insert is assembled into the shell.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1 is an exploded perspective view of an acetabular cup assembly according to one embodiment of the present invention.

FIG. 2 is a cross-sectional view of the liner and bearing component of the acetabular cup assembly of FIG. 1 showing the bearing component mounted within the liner.

FIG. 3 is a cross-sectional view of the assembled acetabular cup assembly of FIG. 1.

FIG. 4 is an enlarged cross-sectional view of a portion of the acetabular cup assembly of FIG. 2.

Corresponding reference characters indicate corresponding parts throughout the several views.

DETAILED DESCRIPTION OF THE DRAWINGS

Figure 5:
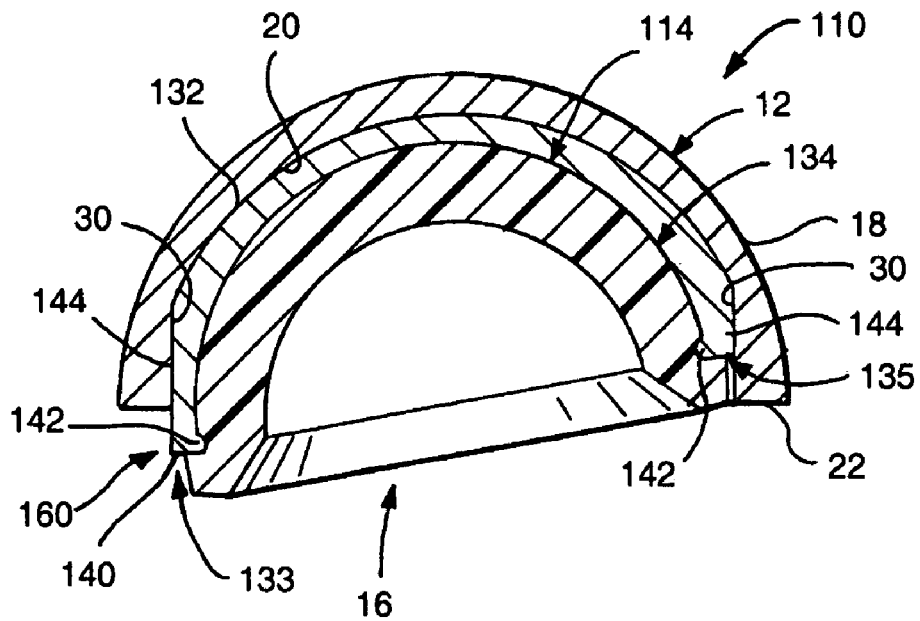
FIG. 5 is a cross-sectional view of an alternative embodiment of an acetabular cup assembly according to the present invention.

An acetabular cup assembly 10 according to one embodiment of the present invention is shown in FIG. 1. Cup assembly 10 includes a shell 12 adapted to be affixed to the acetabulum (not shown) to replace the natural hip socket, a liner 14 adapted to be coupled to shell 12, and a bearing 16 adapted to be coupled to liner 14. Shell 12 includes an outer surface 18 that can be textured to facilitate securing shell 12 in place within an appropriately prepared acetabulum. Shell 12 is preferably made from titanium, but may be made from a cobalt chrome material or other suitable materials. Shell 12 also includes a generally hemispherical shaped inner surface 20. In this specification and in the claims, the words "generally hemispherical" are intended to cover the hemispherical ranges conventionally used in acetabular and glenoid shells, liners, and cup bearings including less than hemispherical and, in some cases, more than hemispherical. Shell 12 further includes a rim 22. Rim 22 defines a plane through which liner 14 and bearing 16 enter a cavity 24 of shell 12 formed by inner surface 20. Inner surface 20 of shell 12 is formed to include a side wall 26 providing, at its outer extent 28 a female taper 30. Female taper 30 extends around the entire periphery of cavity 24 adjacent rim 22. It is understood that the axial depth of female taper 30 within cavity 24 may vary.

Liner 14 includes an outside spherical surface 32 having a male taper 44 that is sized to engage and lock with female taper 30. It is understood that the length of male taper 44 may vary, so long as it securely engages female taper 30. Liner 14 is preferably made from titanium, but may be made from a cobalt chrome material, or other suitable materials. Liner 14 includes an inside surface 34 that preferably defines a chamber 36 sized for receiving bearing component 16. Typically, inside surface 34 is generally hemispherical in shape. In addition, projections 53 may extend from inside surface 34 in a spaced-apart relationship relative to one another for secure engagement with bearing component 16. See FIG. 2. Typically, liner 14 includes four projections 53 positioned at approximately 90" relative to one another to prevent rotation of bearing component 16 within chamber 36. Liner 14 further includes an outer rim 40. Preferably, a locking tab 42 extends into chamber 36 from inside surface 34 adjacent outer rim 40. See FIG. 2.

Referring again to FIG. 1, bearing 16 includes an outer surface 52 that is generally hemispherical in shape. Bearing 16 also includes an inner bearing surface 54 that defines an opening 55 sized to receive a prosthetic femoral ball (not shown). A rim 56 extends circumferentially around opening 55 of bearing 16. Bearing 16 is symmetrical. It is understood, however, that bearing 16 of the present invention may be a nonsymmetrical component. Bearing 16 further includes a circumferential groove 58 spaced apart from rim 56 and sized to receive locking tab 42 of liner 14. Bearing 16 is preferably made from a polymeric material such as ultra high molecular weight polyethylene (UHMWPE). Of course, bearing 16 could be made of other types of implantable bearing materials such as a metal material or a ceramic material.

As shown for example in FIG. 2 bearing 16 may be selectively coupled to liner 14 to form a subassembly 60 in accordance with a kit of the present invention. The user will receive the kit that includes shell 12, and at least two bearing/liner subassemblies 60, 160, 260 such as, for example of the types shown in FIGS. 2, 5 and 6 respectively. Once the user has affixed shell 12 to an appropriately prepared acetabulum, appropriate subassembly 60, 160, 260 for use with the environment may be selected.

Referring now to FIG. 2, to form subassembly 60 of the kit of the present invention, bearing 16 is press-fit into chamber 36 of liner 14. Inside surface 34 of liner 14 has an inner radius 66 that is less than a normal predetermined radius 64 (FIG. 1) of outer surface 52 of bearing 16. Therefore, prior to assembly, bearing 16 is cooled to a temperature that causes its outer surface 52, to shrink in size to a reduced second radius (not shown). It is understood that the amount of size reduction will vary depending upon the material used to construct bearing component 16 and the temperature to which bearing 16 is cooled. Typically, bearing 16 is cooled in liquid nitrogen, however other common refrigeration methods may be used. Therefore, once normal pre-determined radius 64 of outer surface 52 has been reduced, bearing 16 is press-fit into chamber 36 of liner 14. Circumferential groove 58 is generally aligned with locking tab 42 of liner 14. After circumferential groove 58 and locking tab 42 are aligned, bearing 16 is warned to a temperature sufficient to return outside surface 52 of bearing 16 to a size approaching its normal pre-determined radius 64. Thus, bearing 16 and liner 14 are fastened together in a fixed and locked position and form bearing/liner subassembly 60.

This subassembly 60 is then inserted into cavity 24 of shell 12 to form assembled acetabular cup assembly 10. See FIG. 3. Once liner 14 is pressed into cavity 24, female and male tapers 30, 44 cooperate to hold subassembly 60 in place. Male taper 44 of liner 14 engages female taper 30 of shell 12 and forms a metal-to-metal locking mechanical connection therebetween. Tapers 30, 44 may be a straight taper, as in FIGS. 2-7, or they may be as a curve of a conic section—circle, ellipse, parabola, hyperbola or the like. If taper 44 of outside surface 32 of liner 14 is straight, taper 30 of side wall 26 of shell 12 is also straight.

Referring now to FIG. 4, tapers 30, 44 are machine tapers that provide a connection that ensures and maintains accurate alignment between shell 12 and liner 14 and permits shell 12 and liner 14 to be separated for reconditioning or for substitution of other parts. Tapers 30, 44 may be a self-holding taper (i.e. self-locking) or a self-releasing taper. Throughout the specification and claims the terms "self-holding" and "self-locking" are defined as male and female tapers that when in engagement with one another, tend to stay in place owing to the taper angle; no other means of holding is required. That is, in the case of straight, symmetric tapers, the included angle between diametrically opposite points on male taper 44 will be greater than zero degrees and less than or equal to about seventeen degrees. As shown in FIG. 4, which illustrates symmetrical tapers 30, 44, an angle 48 between the opposite points on male taper 44 is greater than zero degrees and less than or equal to about seven degrees. A curved locking taper is achieved when the acute angles between tangents to the curve over much of its length and perpendicular to rim 40 are greater than zero degrees and do not exceed about seven degrees. Removal of the male taper from the female taper is accomplished by starting the removal with a drift key or some other positive mechanism.

As used throughout the specification and claims, the term "self-releasing" is distinguished from the term "self-holding" (or "self-locking") by the taper angle that is sufficiently large to make retention of the male taper in the female taper dependent upon a positive locking device, such as the positive pressure from a corresponding femur head against bearing component 16. In the case of straight, symmetric tapers, the included angle between diametrically opposite points on male taper 44 will be about seventeen degrees. The taper fit between male and female tapers 30, 44 serves only to maintain alignment. Self-releasing tapers will release themselves.

An alternative embodiment of acetabular cup assembly 110 is illustrated in FIG. 5. Acetabular cup assembly 110 includes shell 12, a liner 114 that is coupled in shell 12, and bearing 16 coupled to liner 114 to create liner/bearing subassembly 160. Liner 114 includes an outside surface 132 that is formed for engaging inner surface 20 of shell 12, an inside chamber 134, and an outer rim 140 extending about the circumference of liner 114. In addition, a locking tab 142 extends into inside chamber 134 for engagement with bearing 16. As shown in FIG. 5, outside surface 132 includes a male taper 144 that is angled about its circumference to create unequal tapering lengths on opposite sides 133, 135 of liner 114. This angled taper 144 causes liner/bearing subassembly 160 to be positioned in a lipped orientation within shell 12. It is understood that the angle can be varied to create various tapering lengths in order to create multiple orientations for subassembly 160 within shell 12. Such a lipped orientation can be beneficial in certain environments to aid in the prevention of femoral ball dislocation.

Figure 6:
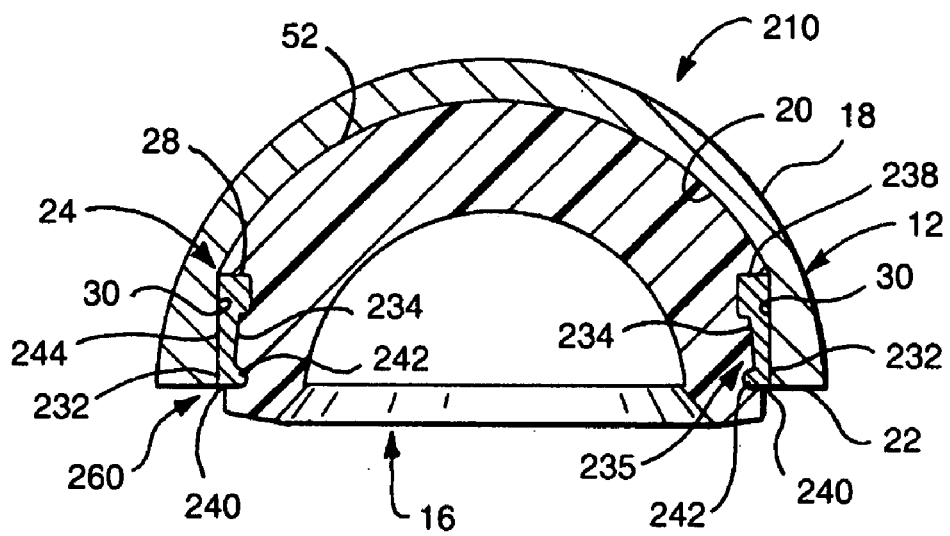
FIG. 6 is a cross-sectional view of an alternative embodiment of an acetabular cup assembly according to the present invention.

Yet another alternative embodiment of acetabular cup assembly 210 is illustrated in FIG. 6. Acetabular cup 210 includes shell 12, a liner 214 that is coupled in shell 12, and bearing 16 coupled to liner 214 to create liner/bearing subassembly 260. Liner 214 is ring-shaped and includes an outside surface 232 that is formed for engaging female taper 30 of shell 12 and an opposite inside surface 234. In addition, liner 214 includes an inner rim 238, an outer rim 240, and an inside chamber 235 extending between rims 238, 240. In addition, a locking tab 242 extends into inside chamber 235 for engagement with outside surface 52 of bearing 16. As shown in FIG. 6, outside surface 232 is formed as a male taper 244 that extends about the circumference. Thus, liner/bearing subassembly 260 when coupled within shell 12 positions bearing, 16 within shell 12.

The taper feature of the present invention provides mechanical lock integrity for the two or three piece construct. This alternative design avoids the need for a metal locking ring and provides a rigid engagement of the liner, essentially eliminating the potential for any relative motion between the metal liner and the metal shell. Without this relative motion, the potential for abrasive wear on an outer surface of the bearing is substantially eliminated. Moreover, a liner that includes a tapered portion helps push the bearing into a pre-determined position and inhibits wear debris from escaping from the liner into the patient.

Additionally, the taper feature of the present invention may be applied to a wide variety of metal liner/plastic bearing subassemblies to create an infinite selection of bearing configurations within the metal shell. This feature is quite advantageous for surgeons who must select a proper configuration of the bearing component relative to a femur head during a surgical procedure. Preferably, each subassembly is infinitely adjustable within the shell to create a variety of orientations suitable for preventing dislocation of the corresponding femur head. Thus, the surgeon must only select a suitable bearing orientation relative to the femur head and press the subassembly in place to engage the corresponding tapers. Once the tapers are engaged, the acetabular cup assembly is automatically and easily held in place.

In addition, FIGS. 7-15 show still another embodiment of the present invention. In particular, FIGS. 7-9 disclose a shell 300 and FIGS. 10-15 disclose a bearing 302 which, when assembled together, collectively creates another acetabular cup assembly which incorporates the features of the present invention therein. The acetabular cup assembly which is made up of the components shown in FIGS. 7-15 is assembled by inserting the bearing 302 (see FIGS. 10-15) into a cavity 304 defined by the shell 300 in a manner similar to the insertion of the liner/bearing subassembly into the cavity of the shell as described above with respect to the embodiments depicted in FIGS. 1-6. However, it should be noted that the embodiment described with respect to FIGS. 7-15 is a two-piece cup assembly, while each of the embodiments described with respect to FIGS. 1-6 is a three-piece cup assembly.

Figure 7:
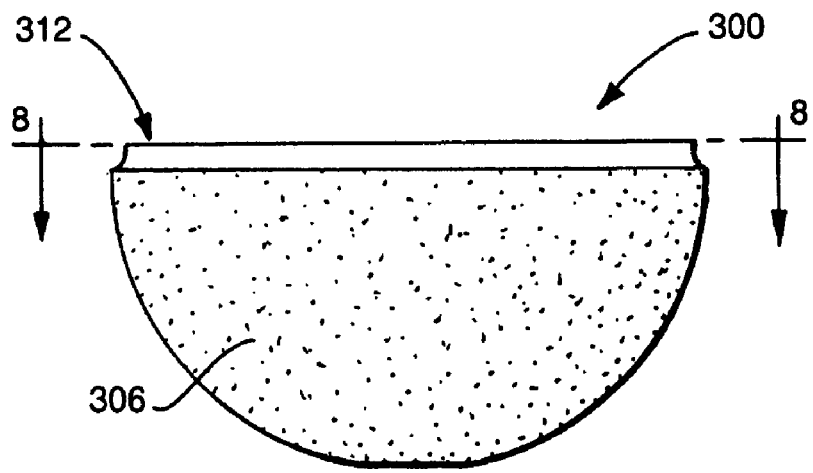
FIG. 7 is an elevational view of a shell which may be assembled with the bearing of FIGS. 10-15 or FIGS. 16-19 to create another acetabular cup assembly which incorporates the features of the present invention therein.

The shell 300 possesses a generally hemispherical shape and is preferably made from a metallic material such as a titanium alloy. Alternatively, the shell 300 may be made from a metallic material such as cobalt chrome. The shell 300 possesses a porous coating 306 located on an outer surface of the shell as shown in FIG. 7. The porous coating 306 is configured to facilitate biological ingrowth of a patient's bone within the outer surface of the shell whereby long-term fixation of the shell 300 to the patient's bone may be achieved. A number of spikes (not shown) may be secured to the outer surface of the shell to further facilitate fixation of the shell 300 to the patient's bone as is well known in the art. An apex hole 308 is defined in the shell 300. The apex hole is provided with a number of threads so as to allow coupling of an insertion instrument (not shown) thereto. The instrument may be coupled to the shell 300 during implantation of the acetabular cup assembly into the patient's body.

Figure 8:
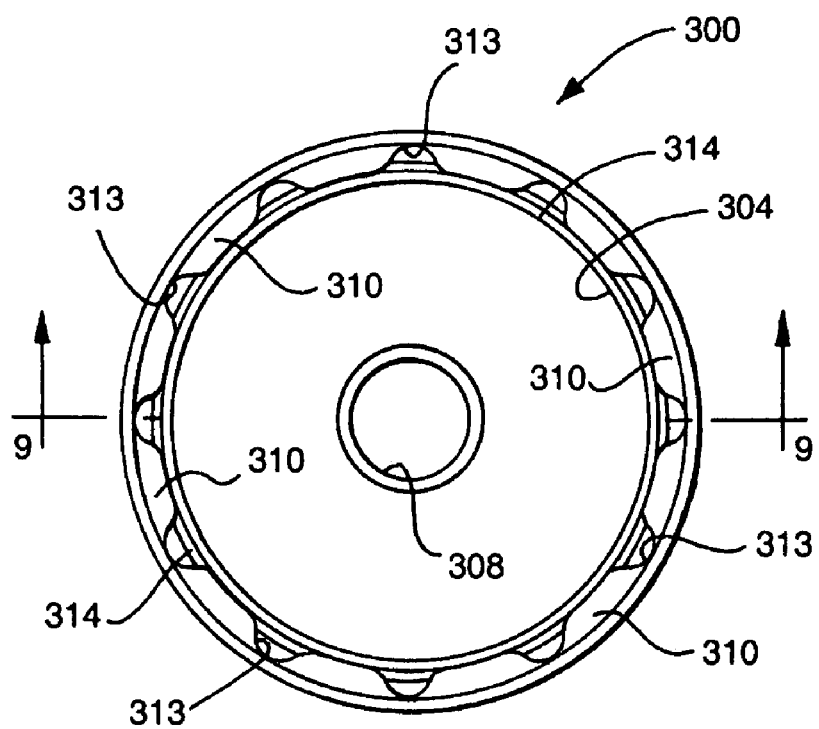
FIG. 8 is an elevational view of the shell of FIG. 7 as viewed in the direction of the arrows 8-8 of FIG. 7.

The shell 300 possesses a plurality of tangs 310 located at an upper rim 312 of the shell 300. Each of the plurality of tangs 310 extends inwardly toward the center of the shell 300 as shown in FIG. 8. The plurality of tangs 310 define a plurality of anti-rotation recesses 313 which are evenly spaced around the upper rim 312 of the shell 300 as shown in FIG. 8. The shell 300 also includes an annular recess 314 which is positioned immediately below the plurality of tangs 310 (see FIGS. 8 and 9).

Figure 9:
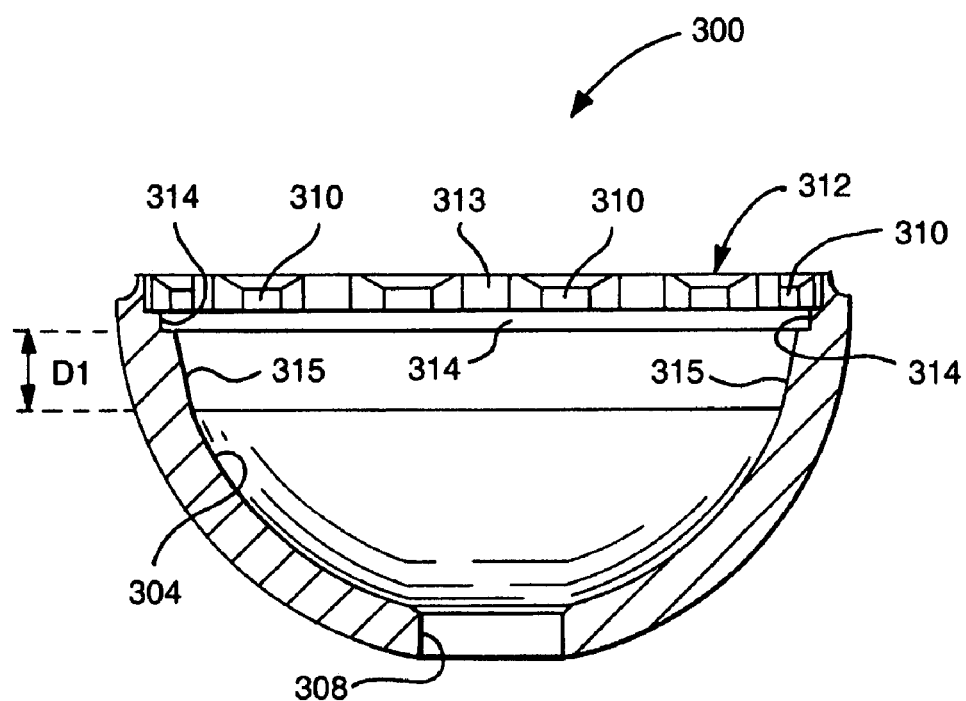
FIG. 9 is a cross-sectional view of the shell of FIG. 8 as viewed in the direction of the arrows 9-9 of FIG. 8.
Figure 10:
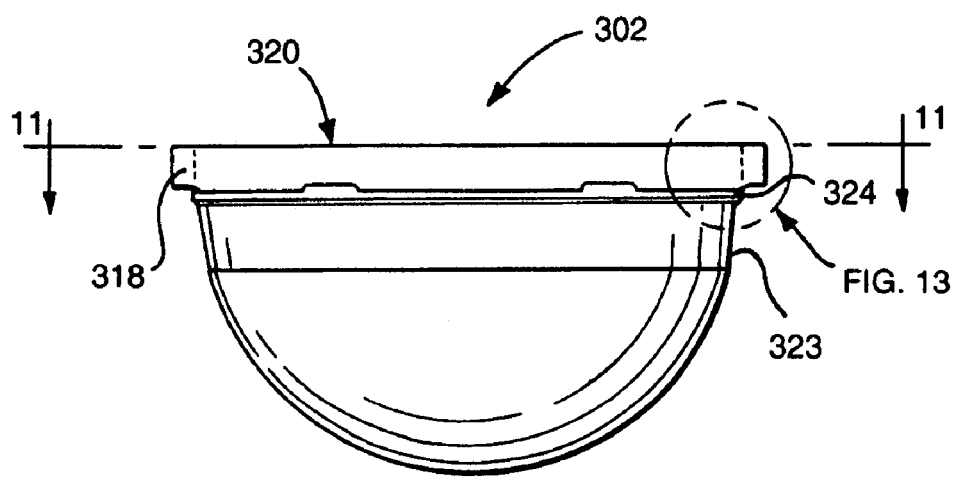
FIG. 10 is an elevational view of a bearing which may be assembled with the shell of FIGS. 7-9 to create an acetabular cup assembly which incorporates the features of the present invention therein.

The shell 300 also includes a female taper 315 which is defined in an inner surface of the shell as shown in FIG. 9. The female taper 315 extends around the entire periphery of the cavity 304 of the shell 300. Moreover, the female taper 315 extends axially for a distance D1 near its upper rim 312 as shown in FIG. 9.

Turning now to FIGS. 10-15, the bearing 302 possesses a generally hemispherical shape and is preferably made from a polymeric material such as ultra high molecular weight polyethylene (UHMWPE). Of course, the bearing 302 could be made of other types of materials which are suitable for implantation into the body of a human being.

Figure 11:
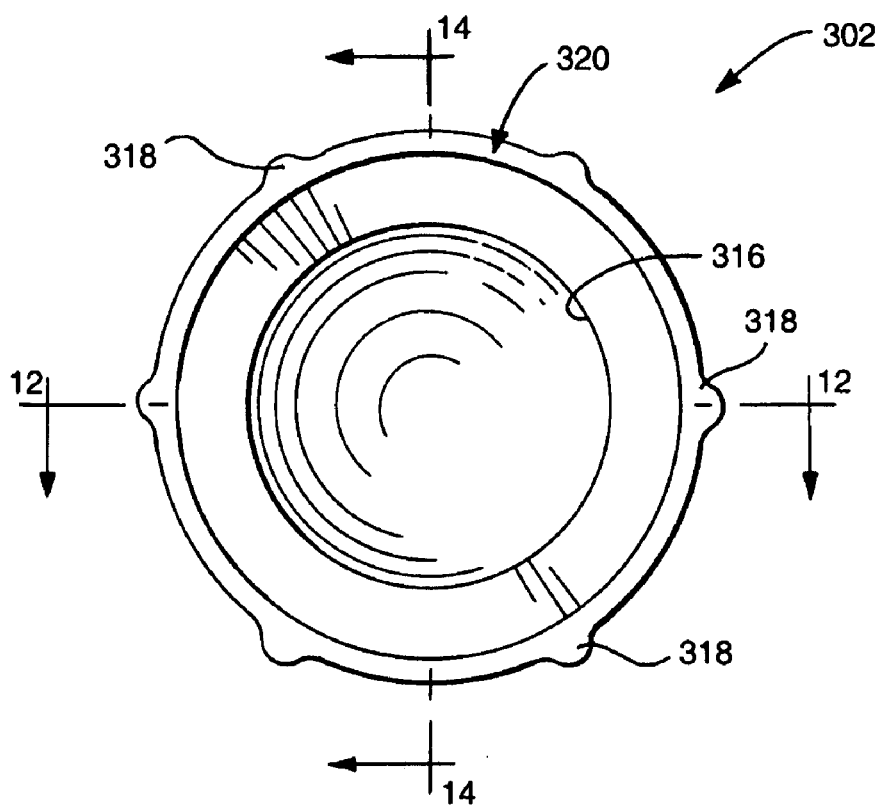
FIG. 11 is an elevational view of the bearing of FIG. 10 as viewed in the direction of the arrows 1-11 of FIG. 10.
Figure 12:
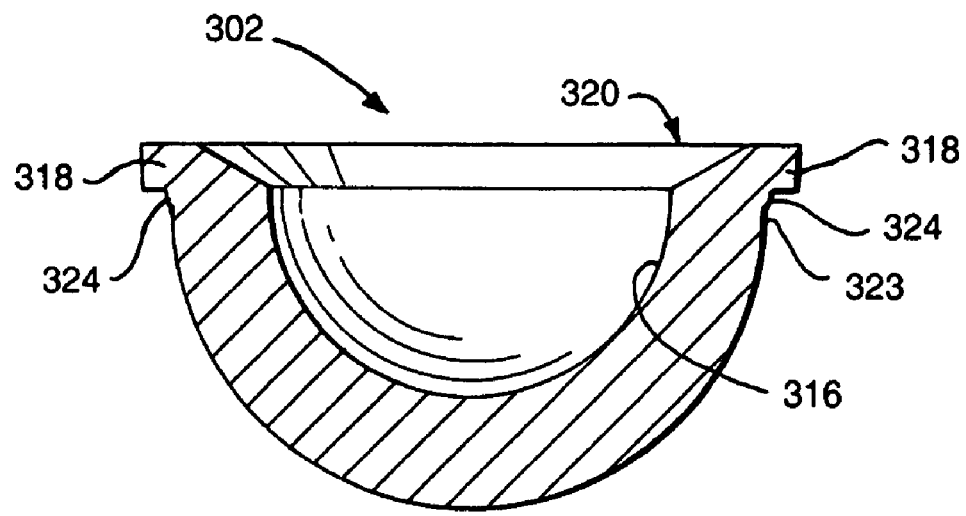
FIG. 12 is a cross-sectional view of the bearing of FIG. 11 as viewed in the direction of the arrows 12-12 of FIG. 11.
Figure 13:
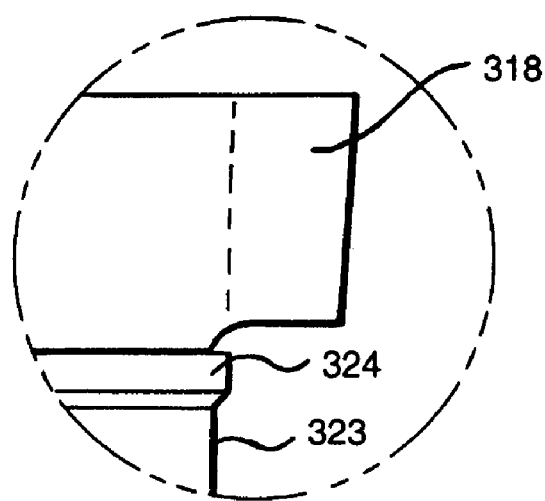
FIG. 13 is an enlarged view of a portion of the bearing of FIG. 10 which is encircled in FIG. 10 and identified as FIG. 13.

The bearing 302 defines a cavity 316 which is configured to receive a prosthetic femoral ball (not shown). The bearing 302 includes a plurality of anti-rotation protrusions 318 which are evenly spaced around an upper rim 320 of the bearing 302 as shown in FIG. 11. Each of the plurality of protrusions 318 extends outwardly away from the center of the bearing 302 as shown in FIG. 11.

Figure 14:
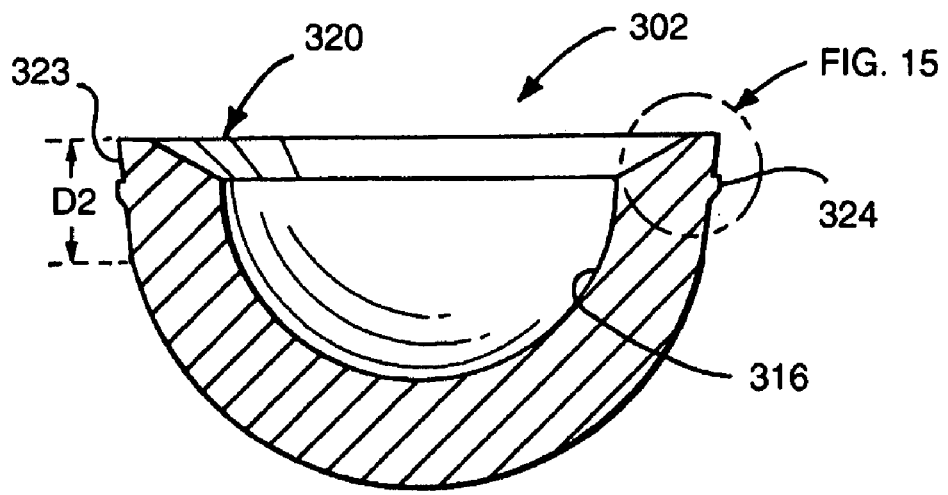
FIG. 14 is a cross-sectional view of the bearing of FIG. 11 as viewed in the direction of the arrows 14-14 of FIG. 11.
Figure 15:
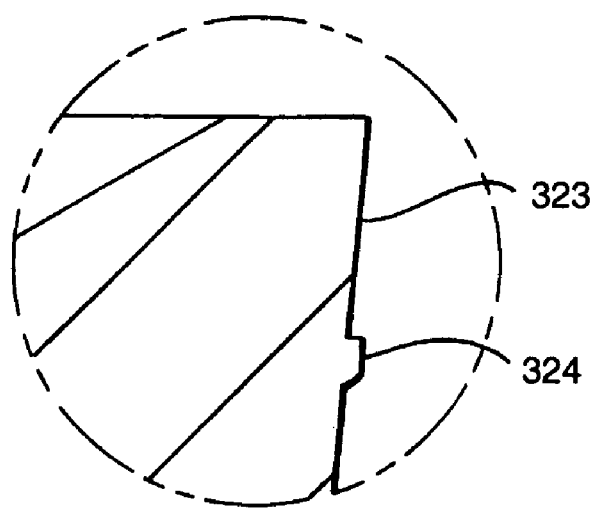
FIG. 15 is an enlarged view of a portion of the bearing of FIG. 14 which is encircled in FIG. 14 and identified as FIG. 15.

The bearing 302 also includes a male taper 323 which is defined in an outer surface of the bearing as shown in FIGS. 10 and 12-15. The male taper 323 extends around the entire periphery of the bearing 302. Moreover, the male taper 323 extends axially for a distance D2 near its upper rim 320 as shown in FIG. 14. The bearing 302 also includes an annular locking member 324 which is located immediately below the plurality of protrusions 318 (see FIGS. 8 and 9). The annular locking member 324 extends around the entire periphery of the bearing 302. The annular locking member 324 extends outwardly from the male taper 323.

When the bearing 302 is positioned in the cavity 304 of the shell 300 after assembly of the acetabular cup assembly made up of the components shown in FIGS. 7-15, the female taper 315 of the shell 300 engages and locks with the male taper 323 of the bearing 302 so as to secure the bearing 302 to the shell 300. Moreover, when the bearing 302 is positioned in the cavity 304 of the shell 300 after assembly of the acetabular cup assembly, the annular locking member 324 of the bearing 302 is located within the annular recess 314 defined in the shell 300 so as to further secure the bearing 302 to the shell 300.

It should be appreciated that the lengths of the female taper 315 and the male taper 323 may vary so long as such lengths are of sufficient magnitude to cause the female taper 315 and the male taper 323 to securely engage each other. Also, in order to achieve appropriate engagement and locking between the female taper 315 of the shell 300 and the male taper 323 of the bearing 302, the taper angle between the two tapers 315, 323 is chosen to be within the range of self-locking tapers. For example, if each taper 315, 323 was in the range of 2°-8.5° (for an aggregate taper angle range of 4°-17°), appropriate engagement and locking between the two components would be achieved.

Moreover, when the bearing 302 is positioned within the cavity 304 of the shell 300 as described above, the plurality of protrusions 318 are respectively positioned within the plurality of recesses 313. With the protrusions 318 positioned within recesses 313, rotational movement of the bearing 302 relative to the shell 300 is inhibited.

FIGS. 16-19 show an alternative bearing 400 which could be substituted for the bearing 302 in order to create yet another acetabular cup assembly which incorporates the features of the present invention therein. Such acetabular cup assembly would cause a cavity 402 of the bearing 400 to be angled with respect to the shell 300 which may be beneficial in certain environments to aid in the prevention of femoral ball dislocation.

Figure 16:
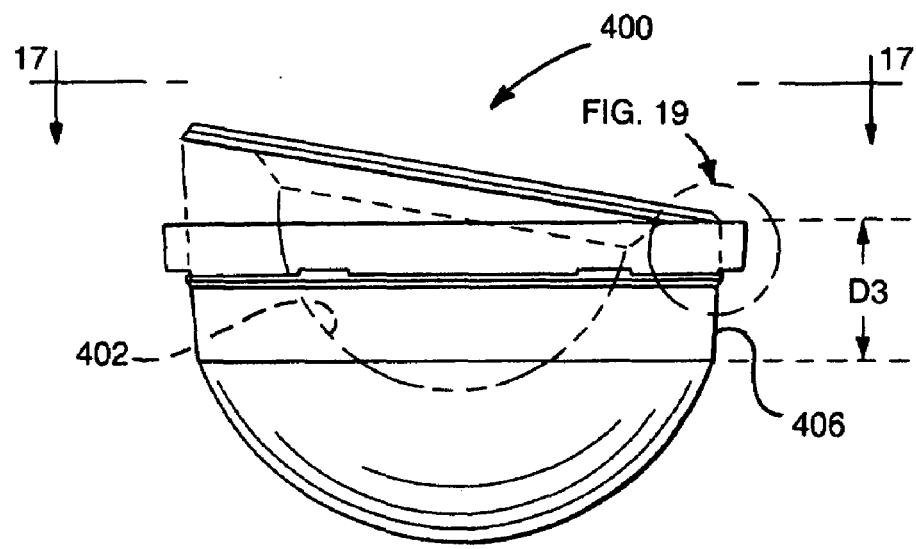
FIG. 16 is an elevational view of alternative bearing which may be assembled with the shell of FIGS. 7-9 to create another acetabular cup assembly which incorporates the features of the present invention therein.
Figure 18:
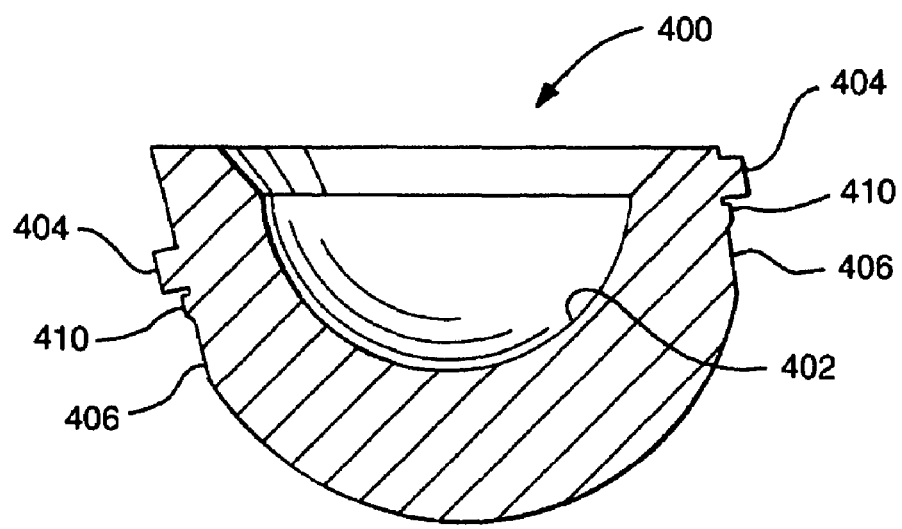
FIG. 18 is a cross-sectional view of the bearing of FIG. 17 as viewed in the direction of the arrows 18-18 of FIG. 17.

The bearing 400 possesses a somewhat hemispherical shape as best shown in FIGS. 16 and 18. The bearing 400 is preferably made from a polymeric material such as ultra high molecular weight polyethylene (UHMWPE). Alternatively, the bearing 400 may be made of other types of materials which are suitable for implantation into the body of a human being such as a metal material or a ceramic material.

Figure 17:
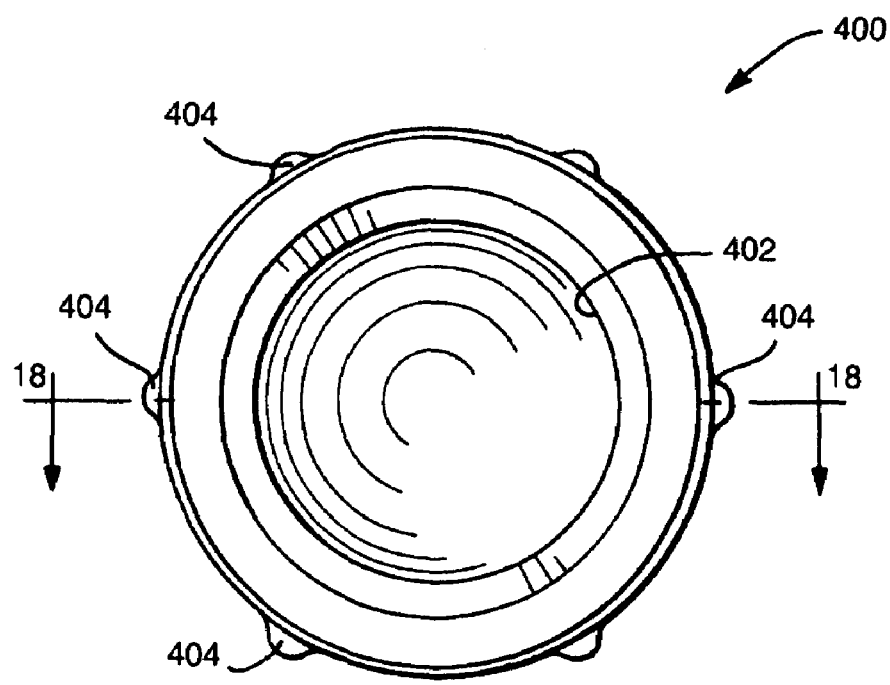
FIG. 17 is an elevational view of the bearing of FIG. 16 as viewed in the direction of the arrows 17-17 of FIG. 16.

The bearing 400 defines the cavity 402 which is configured to receive a prosthetic femoral ball (not shown). The bearing 400 includes a plurality of anti-rotation protrusions 404 which are evenly spaced around the bearing 400 as shown in FIG. 17. Each of the plurality of protrusions 404 extends outwardly away from the center of the bearing 400 as shown in FIG. 17.

Figure 19:
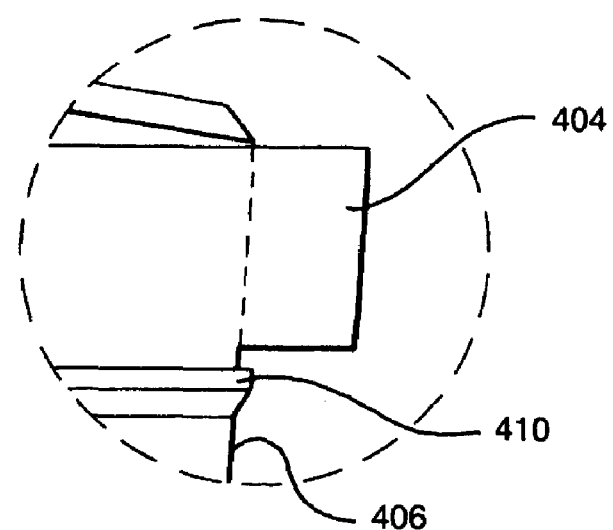
FIG. 19 is an enlarged view of a portion of the bearing of FIG. 16 that is encircled in FIG. 16 and identified as FIG. 19.
Figure 20:
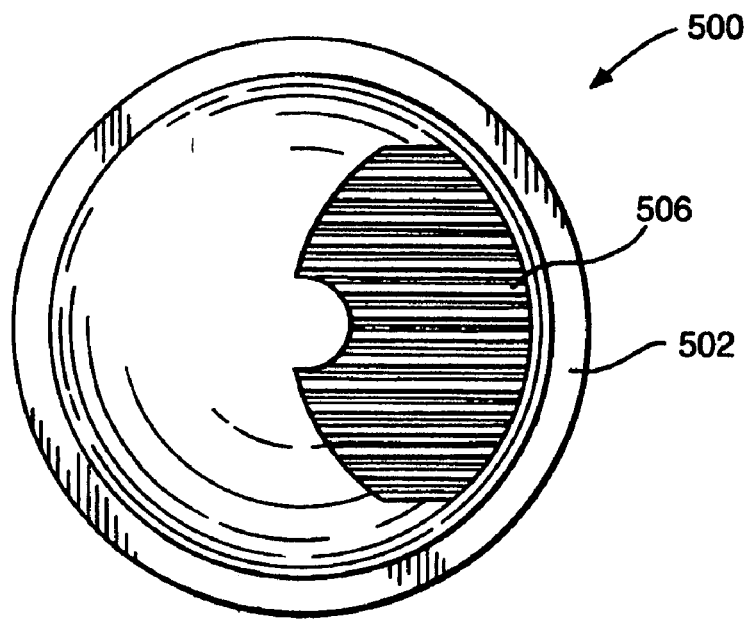
FIG. 20 is top plan view of a prior art acetabular cup assembly illustrating a loading pattern thereon.
Figure 21:
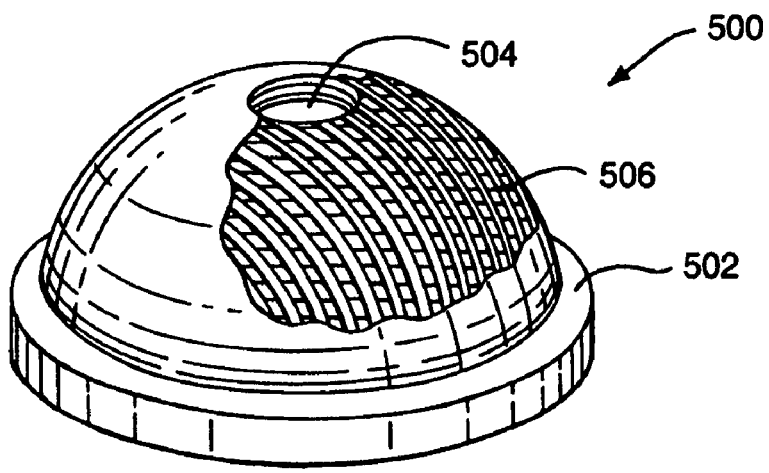
FIG. 21 is a perspective view of the prior art acetabular cup assembly of FIG. 20 illustrating a loading pattern thereon.

The bearing 400 also includes a male taper 406 which is defined in an outer surface of the bearing as shown in FIGS. 16 and 18-19. The male taper 406 extends around the entire periphery of the bearing 400. Moreover, the male taper 406 extends axially for a distance D3 as shown in FIG. 14. The bearing 400 also includes an annular locking member 410 which is located immediately below the plurality of protrusions 404 (see e.g. FIG. 19). The annular locking member 410 extends around the entire periphery of the bearing 400. The annular locking member 410 extends outwardly from the male taper 406.

When the bearing 400 is positioned in the cavity 304 of the shell 300 after assembly of the acetabular cup assembly made up of the components shown in FIGS. 7-9 and 16-19, the female taper 315 of the shell 300 engages and locks with the male taper 406 of the bearing 400 so as to secure the bearing 400 to the shell 300. Moreover, when the bearing 400 is positioned in the cavity 304 of the shell 300 after assembly of the acetabular cup assembly, the annular locking member 410 of the bearing 400 is located within the annular recess 314 defined in the shell 300 so as to further secure the bearing 400 to the shell 300.

It should be appreciated that the lengths of the female taper 315 and the male taper 406 may vary so long as such lengths are of sufficient magnitude to cause the female taper 315 and the male taper 406 to securely engage each other. Also, in order to achieve appropriate engagement and locking between the female taper 315 of the shell 300 and the male taper 406 of the bearing 400, the taper angle between the two tapers 315, 406 is chosen to be within the range of self-locking tapers as described above.

Further, when the bearing 400 is positioned within the cavity 304 of the shell 300 as described above, the plurality of protrusions 404 are respectively positioned within the plurality of recesses 313. With the protrusions 404 positioned within recesses 313, rotational movement of the bearing 404 relative to the shell 300 is inhibited.

Figure 24:
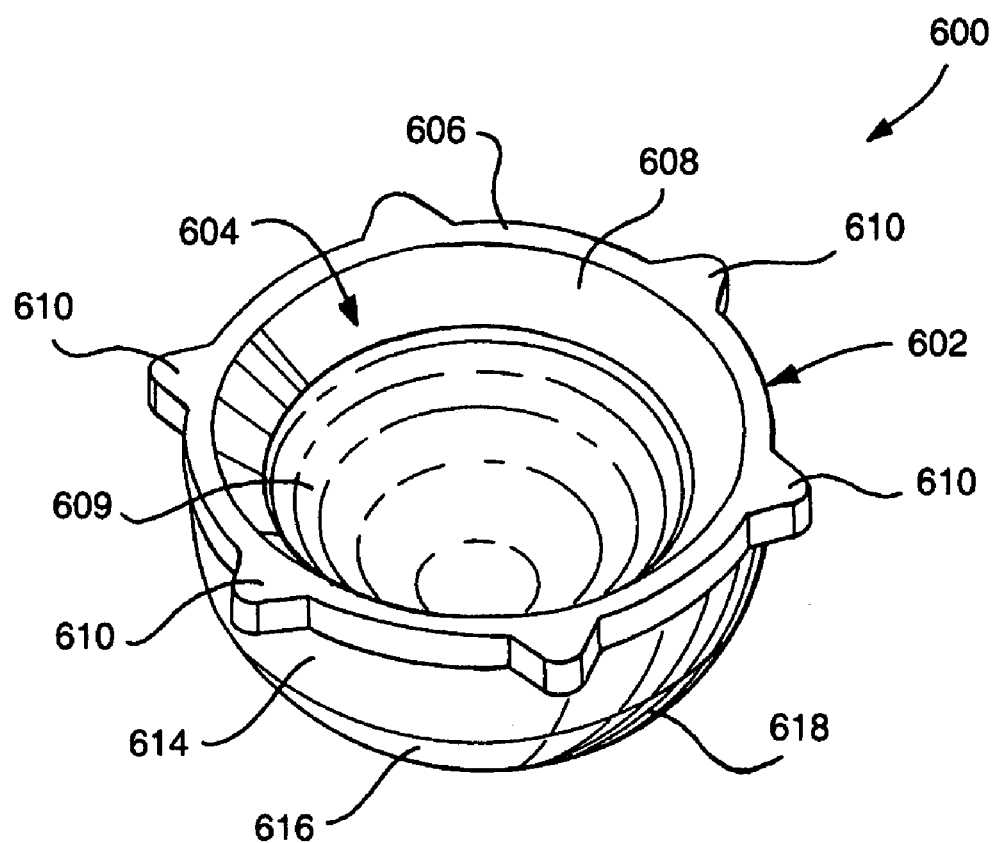
FIG. 24 is a top perspective view of an embodiment of a bearing insert or liner of an acetabular cup assembly that provides the loading pattern shown in FIGS. 22 and 23.

Referring now to FIG. 24 there is depicted another illustrative embodiment of a bearing insert or liner (hereinafter "liner"), generally designated 600, in accordance with principles of the subject invention and shown in a pre-assembled state (i.e. without other components thereof that form a prosthetic assembly). The liner 600 is preferably fabricated from a polymeric material such as plastic. Particularly, the liner 600 is preferably fabricated from the plastic polyethylene. More particularly, the liner 600 is preferably fabricated from an ultra high molecular weight polyethylene (UHMWPE). It should be appreciated, however, that other suitable implantable bearing materials such as a metal material, a ceramic material, or plastics other than polyethylene may be used to fabricate the liner 600. The liner 600 is also preferably formed as one piece.

The liner 600 is formed by a body 602 that has or defines an interior, chamber or cavity 604 and a rim 606 that surrounds an opening of the interior 604. The interior 604 is preferably, but not necessarily semi-hemispherical to hemispherical in shape. The cavity 604 in all cases is configured to accept a head of a prosthetic (not shown) or a head of a bone (not shown). The interior 604 has an angled or ramped portion 608 that extends from the rim 606 into the interior 604. The interior 604 also preferably extends annularly about the top of or opening to the interior 604. The interior 604 also has a dome-shaped or generally hemispherical-shaped surface 609 that begins at an end of the angled portion 608.

The rim 606 may include a plurality of protrusions or projections 610 that are spaced annularly about the rim 606. The protrusions 610 extend generally radially from the rim 606 and aid in preventing rotation of the liner 600 (stabilizing the liner 600) when the liner 600 is assembled as described herein. While the liner 600 depicts six (6) protrusions 610, the number of protrusions 610 is essentially arbitrary but are of a number that is enough to provide rotational stability.

The body 602 has a sidewall or wall 618 that has a tapered or angled outer surface portion or outer taper 614 and a dome or a generally hemispherical-shaped portion (outer surface) 616 extending from the outer taper 614. The outer taper 614 may be termed an outside or male taper and preferably, but not necessarily, extends annularly about the entire periphery of the wall 618. In one form, the taper 614 forms an annular band between the generally hemispherical-shaped dome 616 and the rim 602. There may additionally be a band of space between the rim 602 and the taper 614.

The liner 600 may be fabricated in different sizes to accommodate different anatomies of a patient. In one aspect, the cavity 604 of the liner 600 is sized to accommodate different balls or heads of corresponding prosthetics. In another aspect, the body 602 is sized to be accommodated in various sized shells as described herein.

Figure 25:
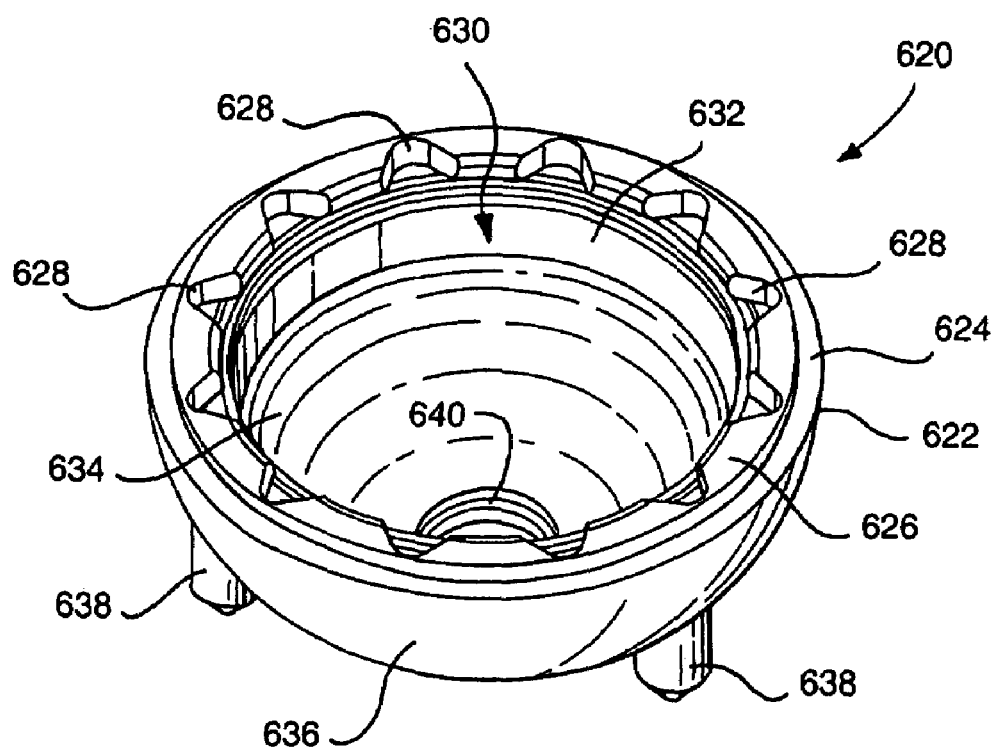
FIG. 25 is a top perspective view of an embodiment of a shell of an acetabular cup assembly that provides the loading pattern shown in FIGS. 22 and 23 when used in conjunction with the bearing insert or liner of FIG. 24.

In FIG. 25 there is depicted another illustrative embodiment of a shell, generally designated 620, in accordance with the principles of the subject invention, and shown in a pre-assembled state (i.e. without other components thereof that form a prosthetic assembly). The shell 620 is adapted to be affixed to the acetabulum of a patient (not shown) to replace the natural hip socket. The shell 620 includes an outer surface 636 that is generally semi-hemispherical to hemispherical in shape. The outer surface 636 can be textured to facilitate securing the shell 620 in place within an appropriately prepared acetabulum (not shown). The shell 620 is preferably made from a metal such as titanium, but may be fabricated from a cobalt chrome material, other metal or other suitable materials. The shell 620 may also include a plurality of pegs, posts, or the like 638 that are adapted to help maintain the shell 620 seated in the appropriately prepared acetabulum. The pegs 638 are optional and thus may or may not be provided.

The shell 620 has an interior, chamber or cavity 630 that has a tapered or angled inner surface or inner taper 632 joined with a generally hemispherical-shaped inner surface 634 extending from an end point of the taper 632. The taper 632 may be termed a female, inside, or inner taper and preferably, but not necessarily, extends annularly about the entire periphery of the cavity 630. The shell 620 also has a rim 626. The rim 626 defines a plane through which the liner 620 enters the cavity 630 when the prosthetic component (constituting in this case, the shell 620 and the liner 600) is assembled. The rim 626 has a plurality of notches or cutouts 628 that are spaced annularly thereabout. The notches 628 correspond in shape to the protrusions 610 of the liner 600 but are a little larger in dimension (width and length) than the protrusions 610. In this manner the protrusions 610 are thus adapted to be received in the notches 628 when assembled.

Figure 26:
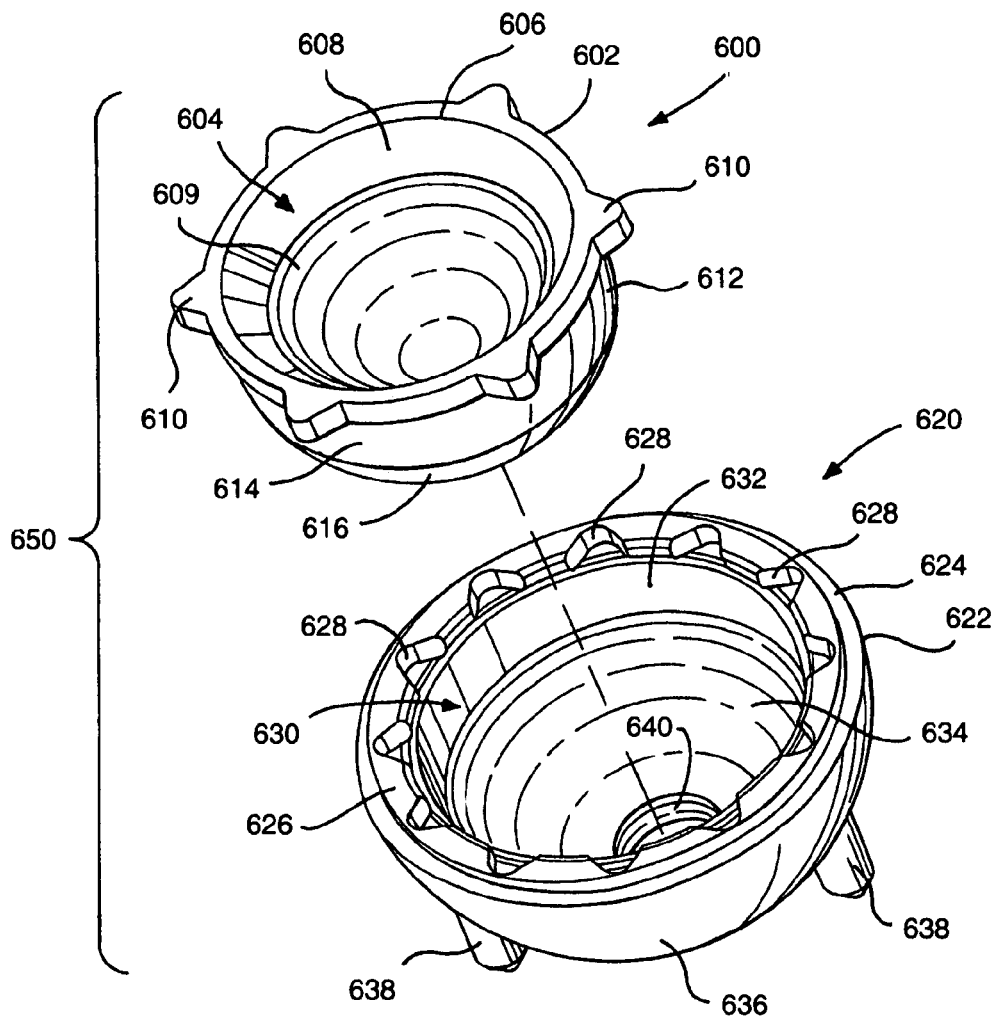
FIG. 26 is an exploded perspective view of the acetabular cup assembly consisting of the bearing insert or liner of FIG. 24 and the shell of FIG. 25.

As shown for example in FIG. 26, the liner 600 is received into the shell 620 to form a prosthetic component assembly (prosthetic assembly) 650. The prosthetic assembly 650 may be provided as a kit. A user (typically a doctor) will receive the kit that includes the shell 620 and the liner 600. The shell and liner are coordinated in size. It should be appreciated however, that the shell and liner assembly come in various sizes to accommodate the various differences in human anatomy. The liner 600 is inserted into the shell 620 at a point in the assembly process.

Specifically, FIG. 26 depicts an exploded view illustrating how the liner 600 fits into or is received by the shell 620 (assembled). It should be appreciated that the exploded view of FIG. 26 is with respect to the shell 620 and the liner 600 and thus is without regard to the shell 620 being affixed to a patient's bone.

Particularly, the liner 600 is received into the cavity 630 of the shell 620. The liner 600 is axially received into the cavity 630 until the outside taper 614 of the liner 600 co-acts with the inside taper 632 of the shell 620 to prevent further axial movement of the liner 600 with respect to the shell 620. The co-action of the tapers 614 and 632 also prevents rotational movement (micro motion) of the liner 600 with respect to the shell 620. The notches 628 and protrusions 610 also prevent rotational movement (macro motion) of the liner 600 with respect to the shell 620. Such co-action of the tapers 614 and 632 locks (preferably releasably) the liner 600 to the shell 620. At this point, the exterior surface 616 of the liner 600 is substantially congruent with the interior surface 634 of the shell 620. Additionally, the protrusions 610 are received in the notches 628, if the liner and shell optionally include such protrusions and notches.

Figure 27:
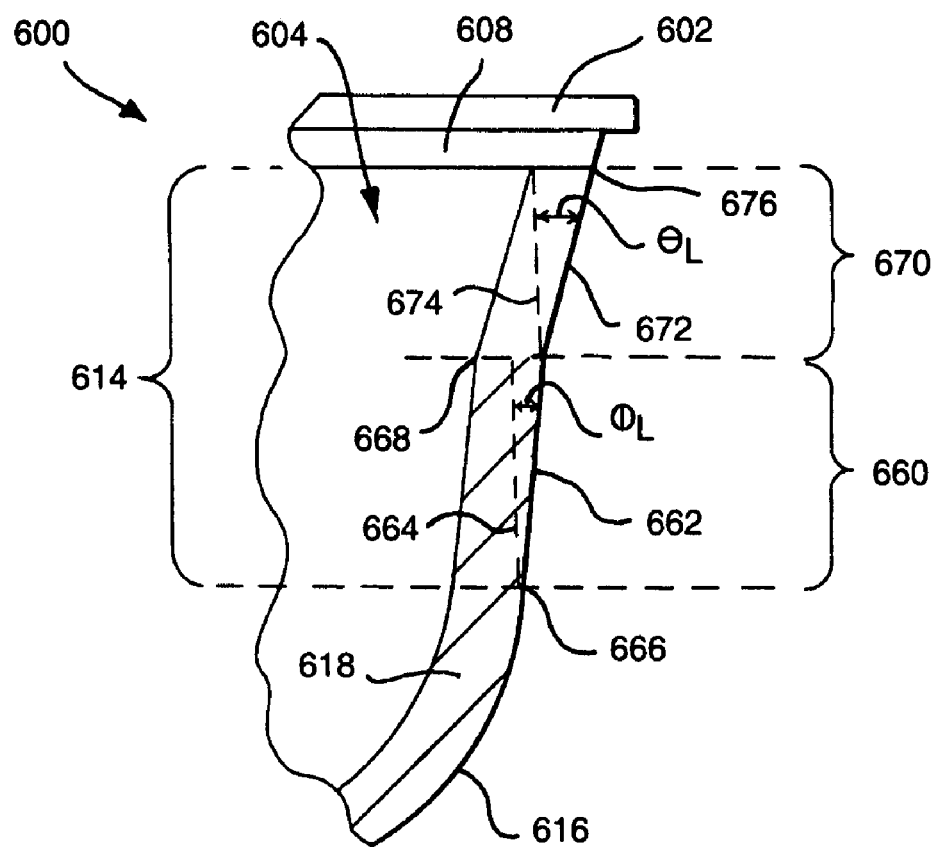
FIG. 27 is an enlarged, partial sectional view of a portion of the wall of the liner of FIGS. 24 and 26 particularly showing the taper thereof.

Referring to FIG. 27, the outer taper 614 of the liner 600 is depicted in a sectional view with regard to a portion of the sidewall or wall 618 of the liner or bearing insert 600. The outer taper 614 is defined between a beginning or commencement point 666 and an end or termination point 676. It should be appreciated that the commencement point 666 and the termination point 676 are arbitrary designations and can be reversed such that the point 676 is the commencement point and the point 666 is the termination point. The commencement point 666 also defines a beginning point for the surface 616.

The thickness of the wall 618 may be substantially constant throughout the length of the taper 614 (wall 618 portion) as well as elsewhere along the length of the wall 618. Alternatively, the thickness of the wall 618 along the length of the taper 614 may be variable. The remaining portions of the wall may have a variable thickness as well. Additionally, the wall 618 of the liner 600, may be formed of variable to constant wall thickness sections. In an exemplary embodiment of a variable thickness wall 618, the taper 614 may be thicker at the termination point 676 than at the commencement point 666. This may be gradual from one point to the other point and thus defines a gradient of thickness for the wall.

In accordance with an aspect of the subject invention, the taper 614 has a first or lower section or portion 660 and a second or upper section or portion 670. Again, it should be appreciated that first and second are arbitrary designations and thus the first may be the second, while the second may be the first. A transition point 668 defines the first and second portions 660 and 670. Particularly, the first portion 660 is defined as between the commencement point 666 and the transition point 668, while the second portion 670 is defined as between the transition point 668 and the termination point 676. The length of each portion 660 and 670 is variable within any constraints discussed herein. However, in accordance with an aspect of the subject invention the lengths of each portion 660 and 670 (defined by the position of the transition or gage point 668 within the taper 614) are preferably within a predetermined proportion with respect to the overall length of the taper 614. Further, with respect to wall thickness, each taper portion 660 and 670 may have their own constant or variable thickness, the variable thickness having a gradient of thickness variation.

It has been determined from a least material condition (LMC) for the prosthetic assembly 650 and a maximum material condition (MMC) for the prosthetic assembly 650 (as described more fully below), that a preferable benchmark or fundamental transition point is approximately ⅔ of the length of the taper 614 relative from the termination point 676. In accordance with this embodiment, the length of the first portion 660 is preferably, approximately ⅓ of the total length of the taper 614, while the length of the second portion 670 is preferably, approximately ⅔ of the total length of the of the taper 614. This may also be considered a baseline or fundamental position to which other lengths of the outer taper portions 660 and 670 and the overall length of the outer taper 614 are considered.

Regardless of the length of the taper 614 and of the taper portions 660 and 670, a first outer surface 662 of the taper portion 660 is at an angle $\phi_L$ with respect to a vertical 664, while a second outer portion surface 672 of the taper portion 670 is at an angle $\theta_L$ with respect to a vertical 674. The verticals 672 and 674 are parallel such that the angles $\phi_L$ and $\theta_L$ are definable from a common (translatable) vertical. The angles $\phi_L$ and $\theta_L$ are non-zero, where a zero angle is defined as parallel to or congruent with the verticals 672 and 674.

The first outer surface 662, between points 666 and 668, defines an angle $\varnothing_L$ from the vertical 664. The angle $\varnothing_L$ is radially outward of the interior 604. The angle $\varnothing_L$ is preferably between 0° and 22.5° inclusive ($0° \leq \varnothing_L \leq 22.5°$). The second outer surface 672, between points 668 and 676, defines an angle $\theta_L$ from the vertical 674. The angle $\theta_L$ is radically outward of the interior 604. The angle $\theta_L$ is preferably between 0° and 22.5° inclusive ($0° \leq \varnothing_L \leq 22.5°$). The angles $\varnothing_L$ and $\theta_L$ also preferably have a relationship wherein the angle $\theta_L$ is equal to or greater than the angle $\varnothing_L$ ($\varnothing_L \geq \theta_L$). The second outer surface 672 (the outer surface of the second outer taper portion 670) is preferably at an angle $\theta_L$ that is greater than the angle $\varnothing_L$ of the first outer surface 662 (the outer surface of the first outer taper portion 660).

Figure 28:
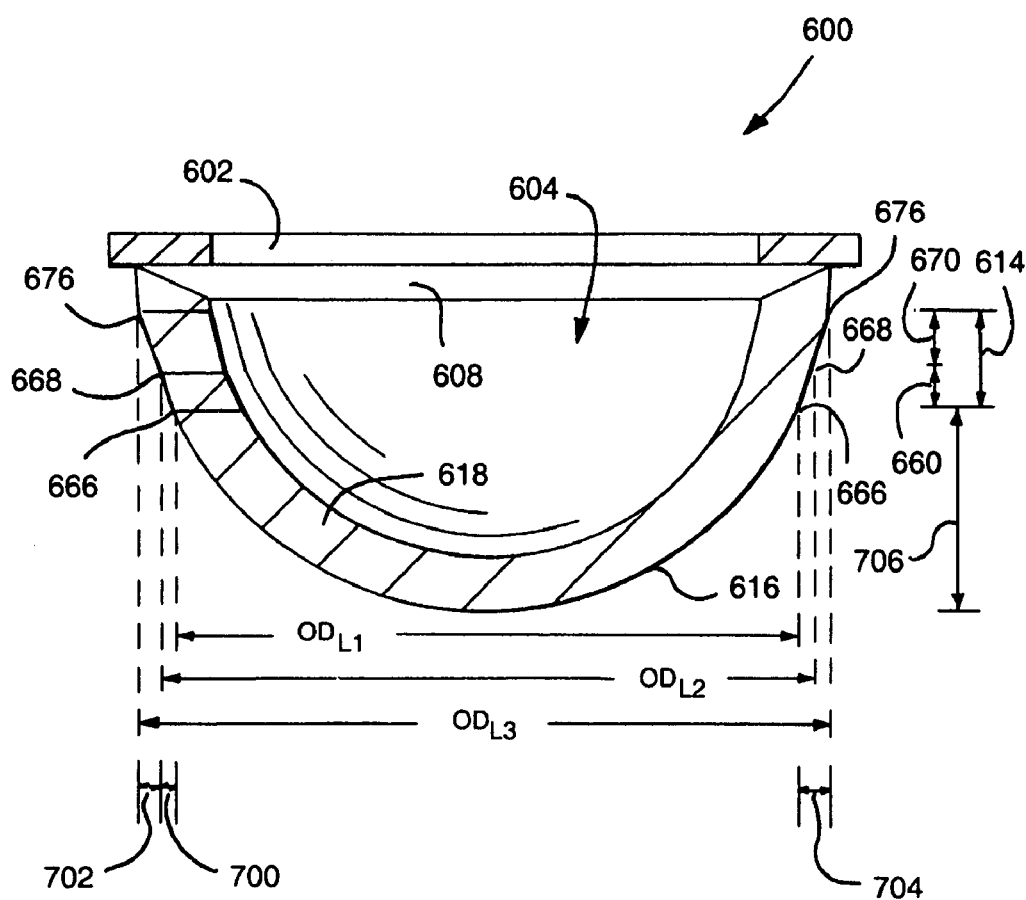
FIG. 28 is a sectional view of the liner.

As seen in FIG. 28, the first outer surface 662 of the first taper portion 660 may also be described in terms of outer diameters of the various points of the first outer surface 662 of the first taper portion 660. The first outer surface 662 has an outer diameter $OD_{L1}$ that is defined from the commencement point 666 on one side of the liner 600 and the commencement point 666 on the other side (180° thereof) of the liner 600, and an outer diameter $OD_{L2}$ that is defined from the transition point 668 at one side of the liner 600 and the transition point 668 on the other side (180° thereof) of the liner 600. The outer diameters $OD_{L1}$ and $OD_{L2}$ have a relationship of $OD_{L1} < OD_{L2}$. A positive slope or gradient 700 of outer diameters is thus defined between the outer diameters $OD_{L1}$ and $OD_{L2}$.

The first taper portion 660 can also be considered a first conic portion (a truncated cone section) defined by two parallel planes (one plane defined as through the commencement points 666, and the other plane defined as through the transition points 668) intersecting a cone, the two planes being parallel to a base of the cone. The cone has a side surface having an angle corresponding to the angle ($\phi_L$) of the first outer surface 662.

The second outer surface 672 of the second taper portion 670 may also be described in terms of outer diameters of the various points of the second outer surface 662 of the second taper portion 670. The second outer surface 662 has an outer diameter $OD_{L2}$ that is defined from the transition point 668 at one side of the liner 600 and the transition point 668 on the other side (180° thereof) of the liner 600, and an outer diameter $OD_{L3}$ that is defined from the termination point 676 on one side of the liner 600 and the termination point 676 on the other side (180° thereof) of the liner 600. The outer diameters $OD_{L2}$ and $OD_{L3}$ have a relationship of $OD_{L2} < OD_{L3}$. A positive slope or gradient 702 of outer diameters is thus defined between the outer diameters $OD_{L2}$ and $OD_{L3}$.

The second taper portion 670 can also be considered a second conic portion (a truncated cone section) defined by two parallel planes (one plane defined as through the transition points 668, and the other plane defined as through the termination points 676) intersecting a cone, the two planes being parallel to a base of the cone. The cone has a side surface having an angle corresponding to the angle ($\theta_L$) of the second outer surface 672.

Overall, the outer taper 614 may be described in terms of outer diameters of the various points of the outer taper 614. Particularly, the outer taper 614 may be defined as a plurality of outer diameters from the points of the outer surface 662 between the outer diameters $OD_{L1}$ to $OD_{L3}$. The outer diameters $OD_{L1}$ to $OD_{L3}$ have a relationship of $OD_{L1} < OD_{L3}$ and thus define a positive slope or gradient 704 of outer diameters therebetween. The slope of the outer diameters may change (become greater) at the transition point 668 if the angle $\emptyset_L$ is greater than the angle $\emptyset_L$ ($\theta_L > \emptyset_L$).

Figure 29:
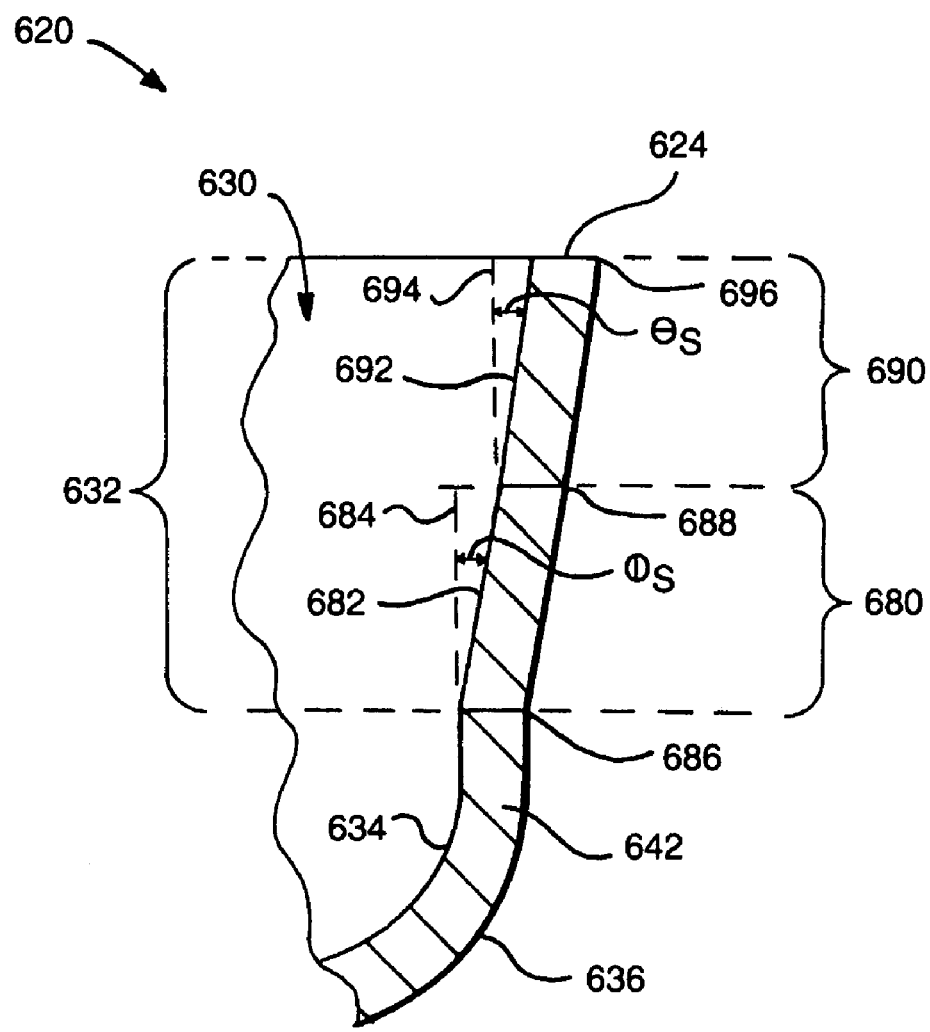
FIG. 29 is an enlarged, partial sectional view of a portion of the wall of the shell of FIGS. 25 and 26 particularly showing the taper thereof.

Referring to FIG. 29 the inner taper 632 of the shell 620 is depicted in a sectional view with regard to a portion of the sidewall or wall 642 of the shell 620. The inner taper 632 is defined between a beginning or commencement point 686 and an end or termination point 696. It should be appreciated that the commencement point 686 and the termination point 696 are arbitrary designations and can be reversed such that the point 696 is the commencement point and the point 686 is the termination point. The commencement point 686 also defines a beginning point for the surfaces 636 and 634.

The thickness of the wall 642 may be substantially constant throughout the length of the taper 632 (wall 642 portion) as well as elsewhere along the length of the wall 642. Alternatively, the thickness of the wall 642 along the length of the taper 632 may be variable. The remaining portions of the wall may have a variable thickness as well. Additionally, the wall 642 of the shell 620, may be formed of variable to constant wall thickness sections. In an exemplary embodiment of a variable thickness wall 642, the taper 632 may be thicker at the termination point 696 than at the commencement point 686. This may be gradual from one point to the other point and thus defines a gradient of thickness for the wall.

In accordance with an aspect of the subject invention, the taper 632 has a first or lower section or portion 680 and a second or upper section or portion 690. Again, it should be appreciated that first and second are arbitrary designations and thus the first may be the second, while the second may be the first. A transition point 688 defines the first and second portions 680 and 690. Particularly, the first portion 680 is defined as between the commencement point 686 and the transition point 688, while the second portion 690 is defined as between the transition point 688 and the termination point 696. The length of each portion 680 and 690 is variable within any constraints discussed herein. However, in accordance with an aspect of the subject invention the lengths of each portion 680 and 690 (defined by the position of the transition or gage point 688 within the taper 632) are preferably within a predetermined proportion with respect to the overall length of the taper 632. Further, with respect to was thickness, each taper portion 680 and 690 may have their own constant or variable thickness, the variable thickness having a gradient of thickness variation.

It has been determined from a least material condition (LMC) for the prosthetic assembly 650 and a maximum material condition (MMC) for the prosthetic assembly 650 (as described more fully below), that a preferable benchmark or fundamental transition point is approximately ⅔ of the length of the taper 632 relative from the termination point 696. In accordance with this embodiment, the length of the first portion 680 is preferably, approximately ⅓ of the total length of the taper 632, while the length of the second portion 690 is preferably, approximately ⅔ of the total length of the of the taper 632. This may also be considered a baseline or fundamental position to which other lengths of the inner taper portions 680 and 690 and the overall length of the inner taper 632 are considered. This also comports with the dimensions of the outer taper 614 of the liner 600.

Regardless of the length of the taper 632 and of the taper portions 680 and 690, a first inner surface 682 of the taper portion 680 is at an angle $\phi_S$ with respect to a vertical 684, while a second inner portion surface 692 of the taper portion 690 is at an angle $\theta_S$ with respect to a vertical 694. The verticals 684 and 694 are parallel such that the angles $\phi_S$ and $\theta_S$ are definable from a common (translatable) vertical. The angles $\emptyset_S$ and $\theta_S$ are non-zero where a zero angle is defined as parallel to or congruent with the vertical 684 and 694.

The first inner surface 682, between points 686 and 688, defines an angle $\phi_S$ from the vertical 684. The angle $\phi_S$ is radially inward toward the cavity 630. The angle $\phi_S$ is preferably between 0° and 22.5° inclusive ($0° \leq \phi_S \leq 22.5°$). The second inner surface 692, between the points 688 and 696, defines an angle $\theta_S$ from the vertical 694. The angle $\theta_S$ is radially inward toward the cavity 630. The angle $\theta_S$ is preferably between 0° and 22.5°, inclusive ($0° \leq \theta_S \leq 22.5°$). The angles $\phi_S$ and $\theta_s$ also preferably have a relationship wherein the angle $\theta_S$ is equal to or greater than the angle $\phi_S$ ($\theta_S = \phi_S$), but may be less than the angle $\phi_S$. The second inner surface 692 (the inner surface of the second inter taper portion 690) is preferably at an angle $\theta_S$ that is the same as the angle $\emptyset_S$ of the first inner surface 682 (the inner surface of the first inner taper portion 680).

Figure 30:
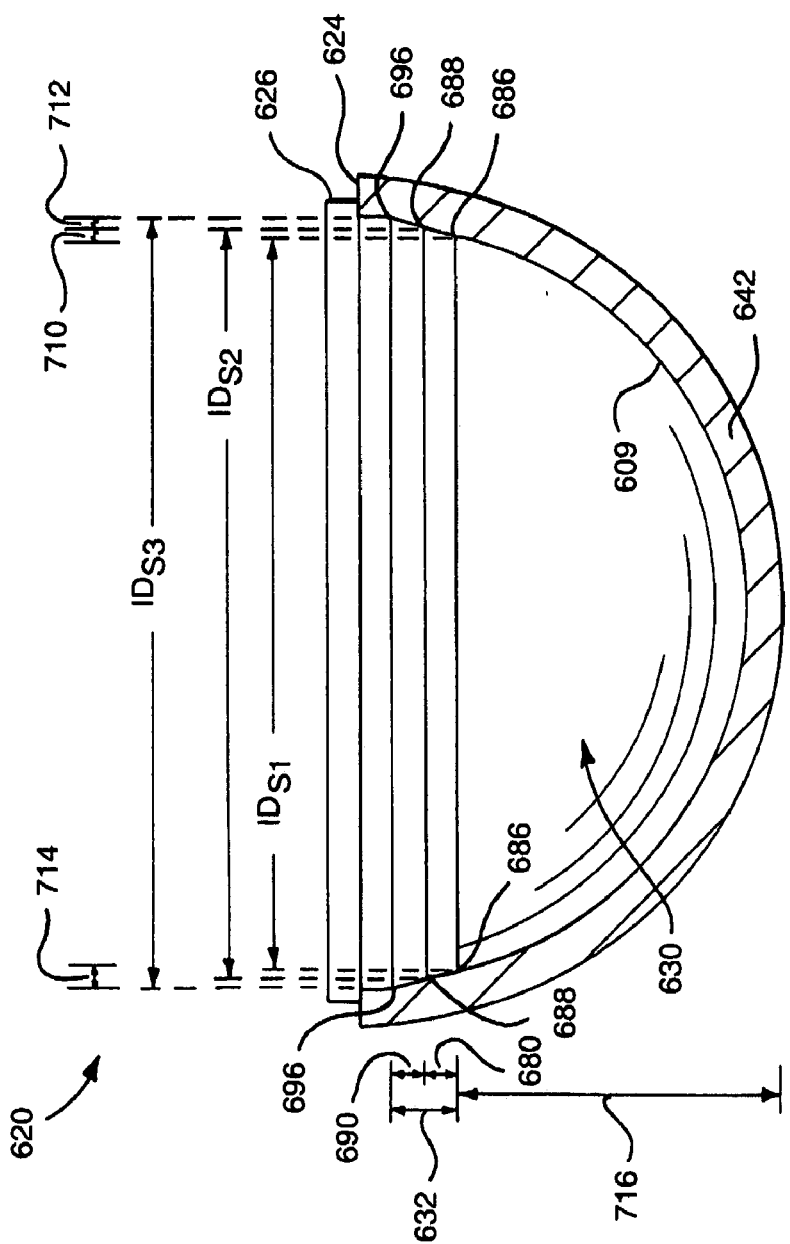
FIG. 30 is a sectional view of the shell.
Figure 31:
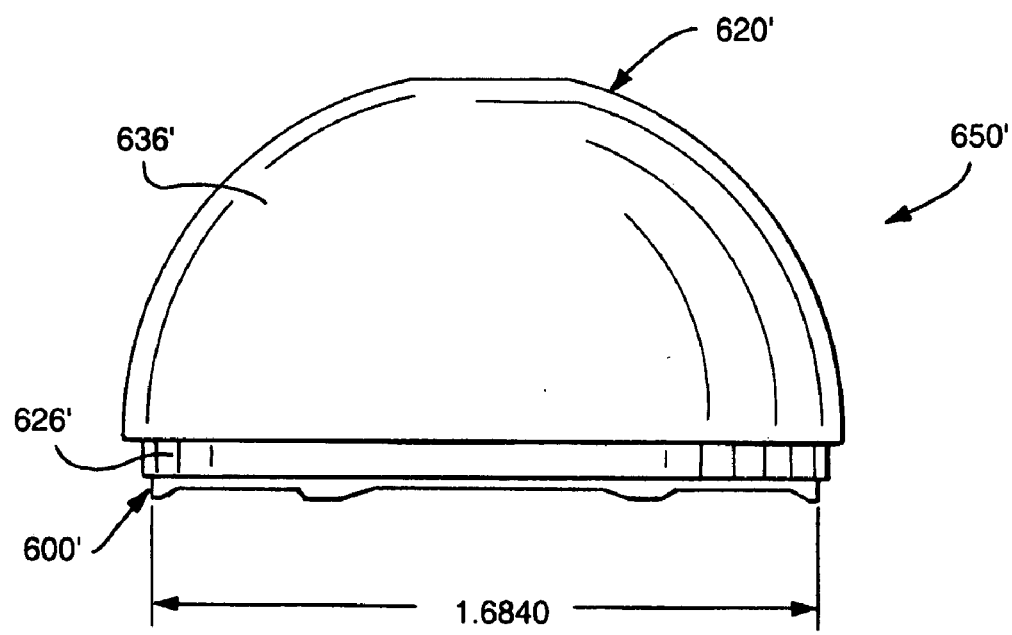
FIG. 31 is an enlarged front elevational view of a maximum material condition embodiment of a prosthetic component assembly in accordance with the principles of the subject invention.
Figure 32:
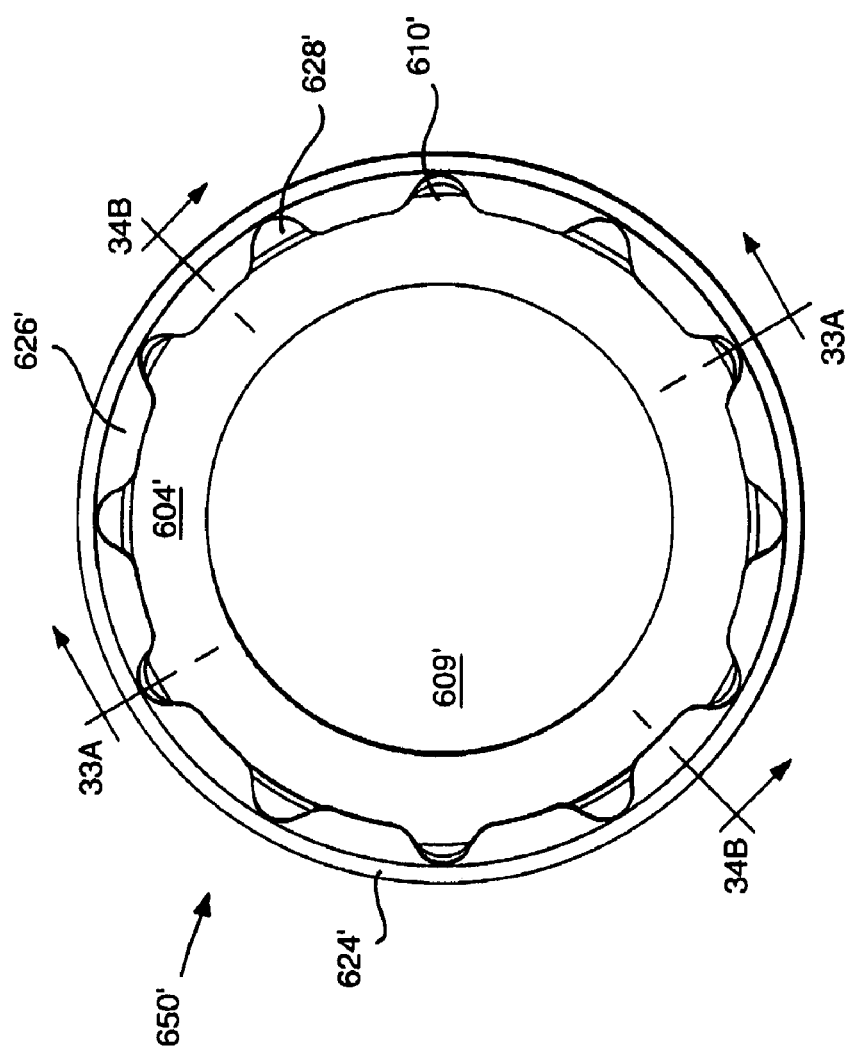
FIG. 32 is a bottom plan view of the prosthetic component assembly of FIG. 31.

As seen in FIG. 30, the first inner surface 682 of the first taper portion 680 may also be described in terms of inner diameters of the various points of the first inner surface 682 of first taper portion 680. The first inner surface 682 has an inner diameter $ID_{S1}$ that is defined from the commencement point 686 on one side of the shell 620 and the commencement point 686 on the other side (180° thereof) of the shell 620, and an inner diameter $ID_{S2}$ that is defined from the transition point 688 at one side of the shell 620 and the transition point 688 on the other side (180° thereof) of the shell 620. The inner diameters $ID_{S1}$ and $ID_{S2}$ have a relationship of $ID_{S1} < ID_{S2}$. A positive slope or gradient 710 of inner diameters is thus defined between the inner diameters $ID_{S1}$ and $ID_{S2}$.

The first taper portion 680 can also be considered a first conic portion (a truncated cone section) defined by two parallel planes (one plane defined as through the commencement points 686, and the other plane defined as through the transition points 688) intersecting a cone, the two planes being parallel to a base of the cone. The cone has a side surface having an angle corresponding to the angle ($\phi_S$) of the first inner surface 682.

The second inner surface 692 of the second taper portion 690 may also be described in terms of inner diameters of the various points of the second inner surface 692 of the second taper portion 690. The second inner surface 692 has an inner diameter $ID_{S2}$ that is defined from the transition point 688 at one side of the shell 620 and the transition point 688 on the other side (180° thereof) of the shell 620, and an inner diameter $ID_{S3}$ that is defined from the termination point 696 on one side of the shell 620 and the termination point 696 on the other side (180° thereof) of the shell 620. The inner diameters $ID_{S2}$ and $ID_{S3}$ have a relationship of $ID_{S2}<ID_{S3}$. A positive slope or gradient 712 of inner diameters is thus detained between the inner diameters $ID_{S2}$ and $ID_{S3}$.

The second taper portion 690 can also be considered a second conic portion (a truncated cone section) defined by two parallel planes (one plane defined as through the transition points 688, and the outer plane defined as through the termination points 696) intersecting a cone, the two planes being parallel to a base of the cone. The cone has a side surface having an angle corresponding to the angle ($\theta_S$) of the second inner surface 692.

Overall, the inner taper 632 may be described in terms of inner diameters of the various points of the inner taper 632. Particularly, the inner taper 632 may be defined as a plurality of inner diameters from the points of the inner surface 682 between the inner diameters $ID_{S1}$ to $ID_{S3}$. The inner diameters $ID_{S1}$ to $ID_{S3}$ have a relationship of $ID_{S1}<ID_{S3}$ and thus define a positive slope or gradient 714 of inner diameters therebetween. The slope of the inner diameters may or may not change at the transition point 688. If the angles $\phi_S$ and $\theta_S$ are the same, the inner taper 632 may be considered as continuous and thus not having two taper portions, The transition or gage point 668 of the liner 600 and the transition or gage point 688 of the shell 620, when assembled, define an essentially zero interference or interference fit between the outer surface at the transition point 668 of the liner 600 and the inner surface at the transition point 688 of the shell 620. The first outer surface 662 (first outer taper portion 660) of the liner 600, when assembled into the shell 620, is either substantially congruent with the first inner surface 682 (first inner taper portion 680) or defines a gap or tolerance (negative interference) between the first outer surface 662 and the first inner surface 682. The gap or tolerance may be constant between the surfaces or may increase between the surfaces. The angle $\phi_L$ of the first outer taper portion 660 is thus equal to or less than the angle $\phi_S$ of the first inner taper portion 680 (i.e. $\phi_L \leq \phi_S$). Further, the outer diameters $OD_{L1}$ and $OD_{L2}$ of the first outer taper portion 660 are essentially equal to or less than the inner diameters $ED_{S1}$ and $ID_{S2}$ respectively of the first inner taper portion 680.

The second outer surface 672 (second outer taper portion 670) of the liner 600, when assembled into the shell 620, provides an interference fit with regard to the second inner surface 692 of the shell. The interference begins at the transition points 668 and 688 of the liner 600 and the shell 620 respectively. The interference fit also depends on the angular relationship of the two angles $\theta_L$ and $\theta_S$. The amount of interference depends on the angle ($\theta_L$ and $\theta_S$) of each respective surface 674 and 692. The angle $\theta_L$ of the second outer taper portion 672 is thus equal to or greater than the angle $\theta_S$ of the second inner taper portion 692 (i.e. $\theta_L \geq \theta_S$). Further, the outer diameters $OD_{L1}$ and $OD_{L2}$ of the first outer taper portion 660 are essentially equal to or less than the inner diameters $ID_{S1}$ and $ID_{S2}$ respectively of the first inner taper portion 680.

It should be appreciated that the shell taper 632 may have a consistent angle throughout its entire length. As such, the shell taper 632 may not be divided or segregated into the two portions 680 and 690. The transition or gage point 688 of the shell taper 632, however, would still provide an interference benchmark or fundamental position for zero (0) interference for the liner 600 and the shell 620 at which point the interference changes. Thus, the transition point 688 of the shell 620 in this particular illustration still provides an alignment with the transition or gage point 668 of the liner 600 when assembled.

Referring to FIGS. 31-36, there is depicted an exemplary embodiment of an assembled prosthetic component generally designated 650'. In addition to depicting an assembled prosthetic component in accordance with the principles of the subject invention, FIGS. 31-36 illustrate a maximum material condition (MMC) and the attendant interference fit relationships between the tapers of the liner and the shell due to the MMC. The MMC provides the most or maximum amount of acceptable interference. The MMC also provides the most or maximum amount of material for the outer diameter of the liner 600' (i.e. the taper is at a maximum thereby producing a maximum outer diameter at the taper).

Figure 33:
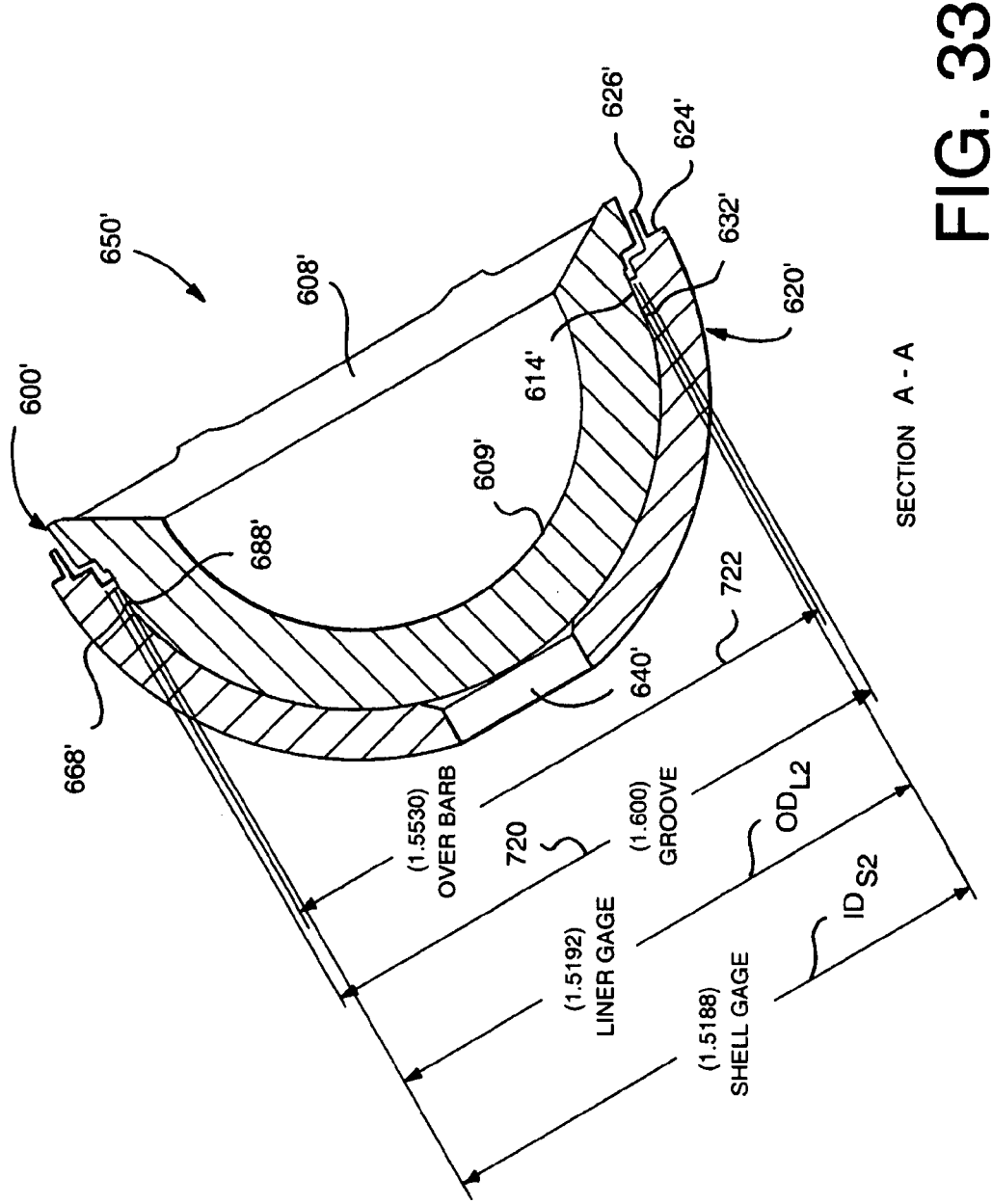
FIG. 33 is a sectional view of the prosthetic component assembly of FIG. 32 taken along line 33A-33A of FIG. 32.

Particularly, the MMC prosthetic component assembly 650' includes a 48 mm outer diameter shell 620' and a 48 mm outer diameter by 28 mm inner diameter liner or bearing insert 600'. As best depicted in FIG. 33, the MMC prosthetic component assembly 650' is such that when assembled, the inner diameter at the shell gage $ID_{S2}$ is slightly smaller than the outer diameter at the liner gage $OD_{L2}$. A groove diameter 720 of the shell 620' has a larger diameter than a barb diameter 722 of the liner 600'.

Figure 34:
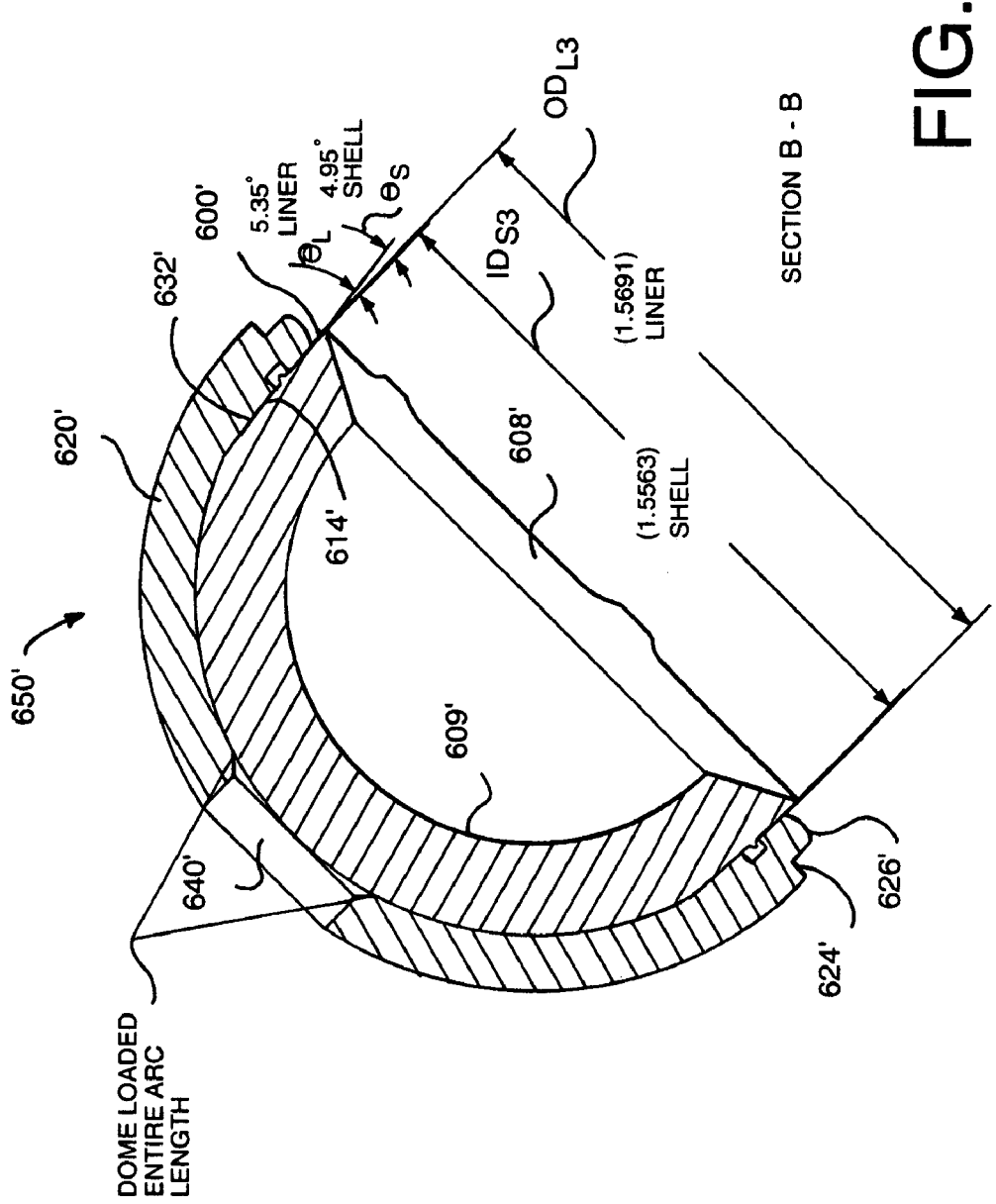
FIG. 34 is a sectional view of the prosthetic component assembly of FIG. 32 taken along line 34B-34B of FIG. 32.

As best depicted in FIG. 34, the angle $\theta_L$ of the liner (here at 5.35°) is greater than the angle $\theta_S$ of the shell (here at 4.95°). This creates an interference fit when assembled between the tapers 614' and 632'. Pre-assembly, the liner 600' has a greater outer diameter ($OD_{L3}$) than the inner diameter ($ID_{S3}$) of the shell 620'.

Figure 35:
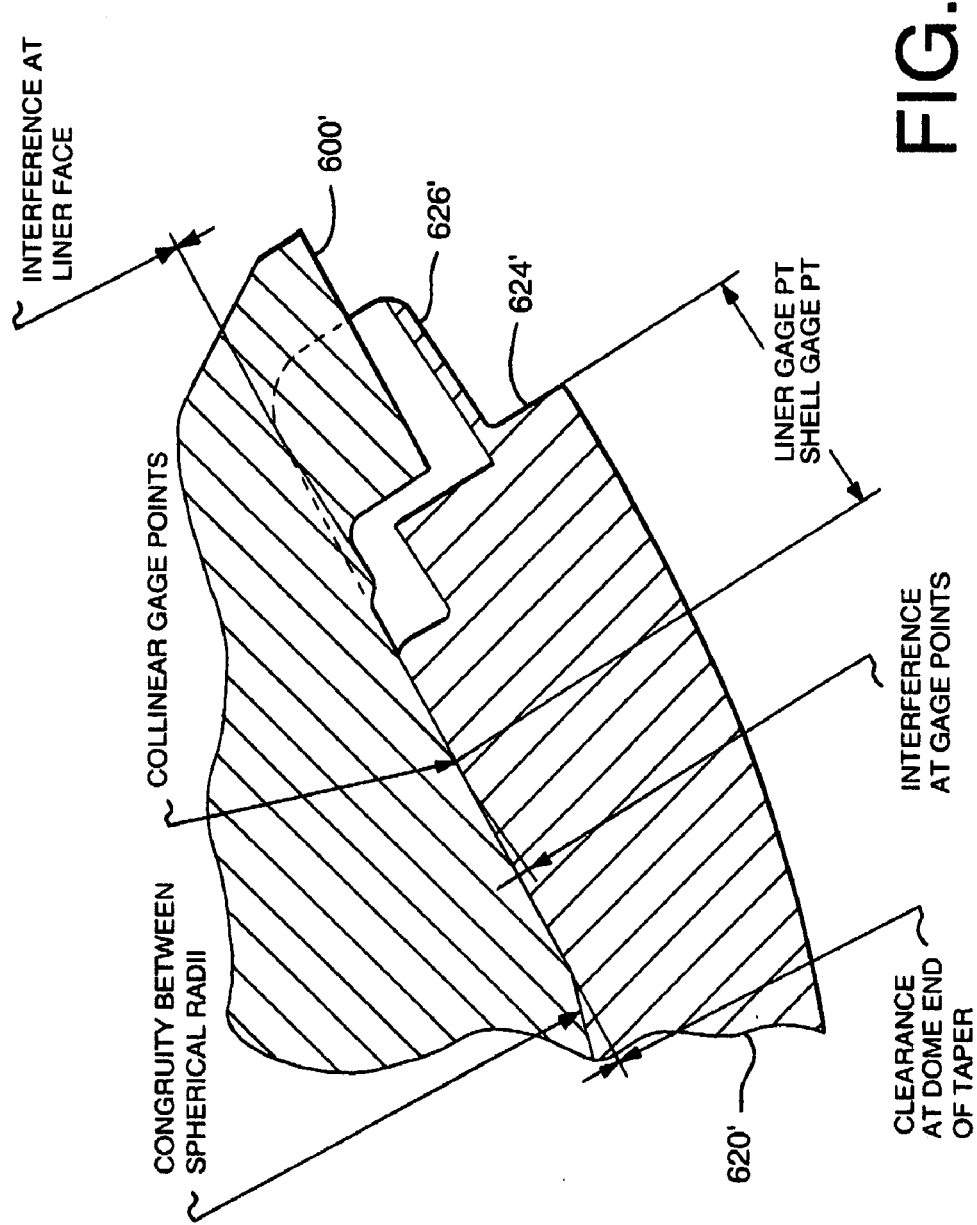
FIG. 35 is an enlarged, partial sectional view of a portion of the prosthetic component assembly of FIGS. 33 and 34 particularly illustrating the maximum material condition interference fit of the bearing insert and shell in accordance with the principles of the subject invention.

Such an interference fit is illustrated in FIG. 35. The interference at the liner face is projected beyond the liner 600' for illustrative purposes. Additionally shown in FIG. 35 is the congruity between the spherical radii of the liner 600' and the shell 620', the collinear gage points, the interference between the liner and shell at the gage points, the clearance at the dome end of the taper, and the position of the liner and shell gage points.

Figure 36:
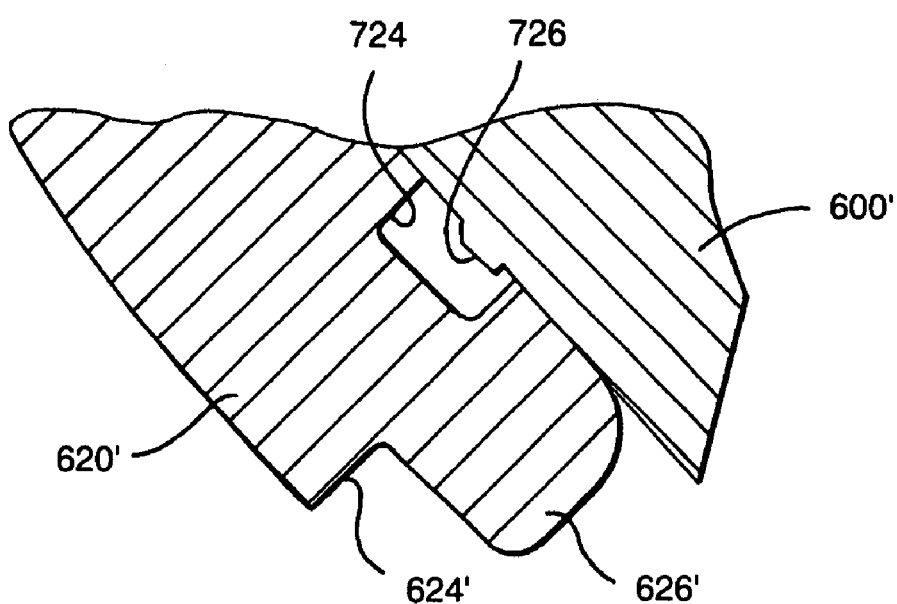
FIG. 36 is an enlarged, partial sectional view of a portion of the prosthetic component assembly of FIGS. 33 and 34 particularly illustrating positioning of a barb of the bearing insert in relation to a channel of the shell.
Figure 37:
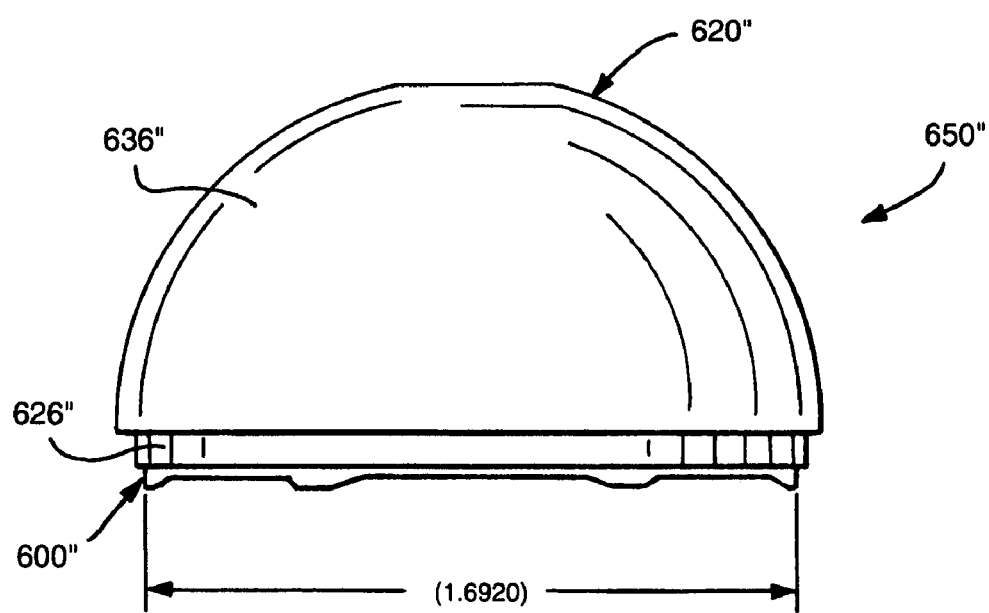
FIG. 37 is an enlarged front elevational view of a least material condition embodiment of a prosthetic component assembly in accordance with the principles of the subject invention.
Figure 38:
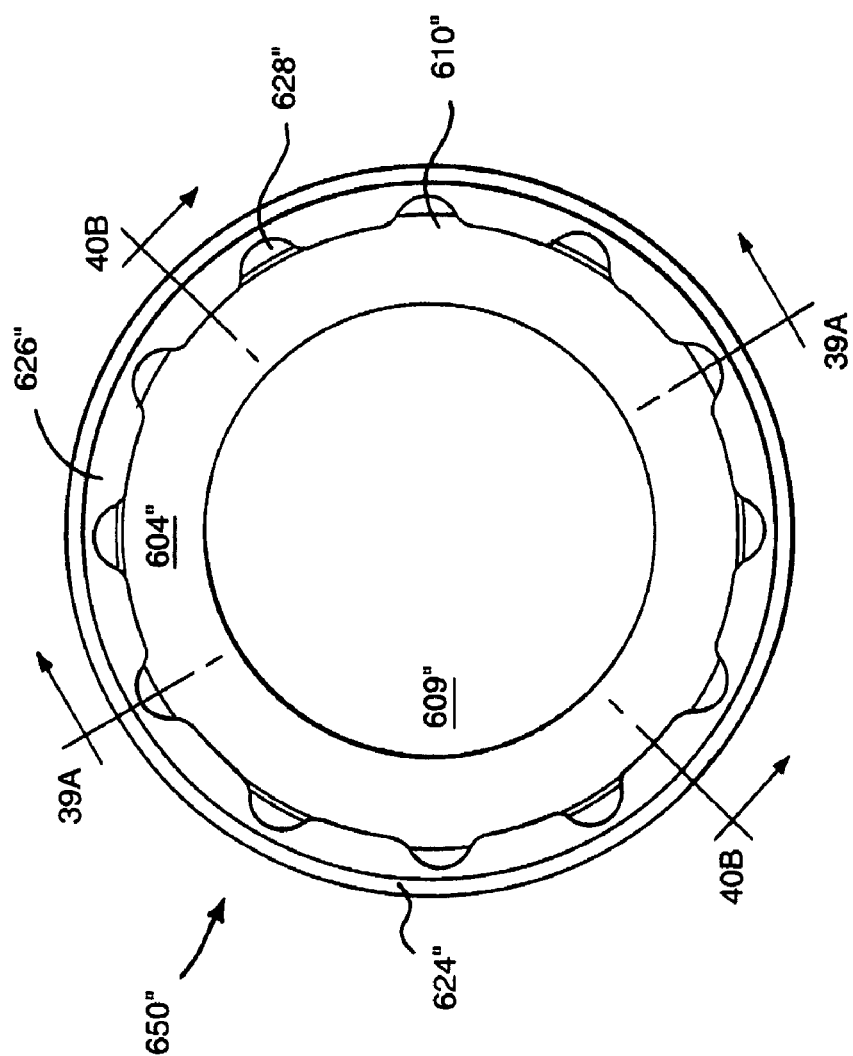
FIG. 38 is a bottom plan view of the prosthetic component assembly of FIG. 37.

In FIG. 36, there is illustrated the channel or groove 724 on the inner surface of the shell 620'. The liner 600' may include a barb 726 that is positioned in the channel 724 when the liner 600' is assembled into the shell 620'.

Referring to FIGS. 37-42, there is depicted an exemplary embodiment of an assembled prosthetic component generally designated 150". In addition to depicting an assembled prosthetic component in accordance with the principles of the subject invention, FIGS. 37-42 illustrate a least material condition (LMC) and the attendant interference fit relationships between the tapers of the liner and the shell due to the LMC. The LMC provides the least or minimal amount of acceptable interference. The LMC also provides the least or minimal amount of material for the outer diameter of the liner 600" (i.e. the taper is at a minimum thereby producing a minimum outer diameter at the taper). Particularly, the LMC prosthetic component assembly 650" includes a 48 mm outer diameter shell 620" and a 48 mm outer diameter by 28 mm inner diameter liner or bearing insert 600".

Figure 39:
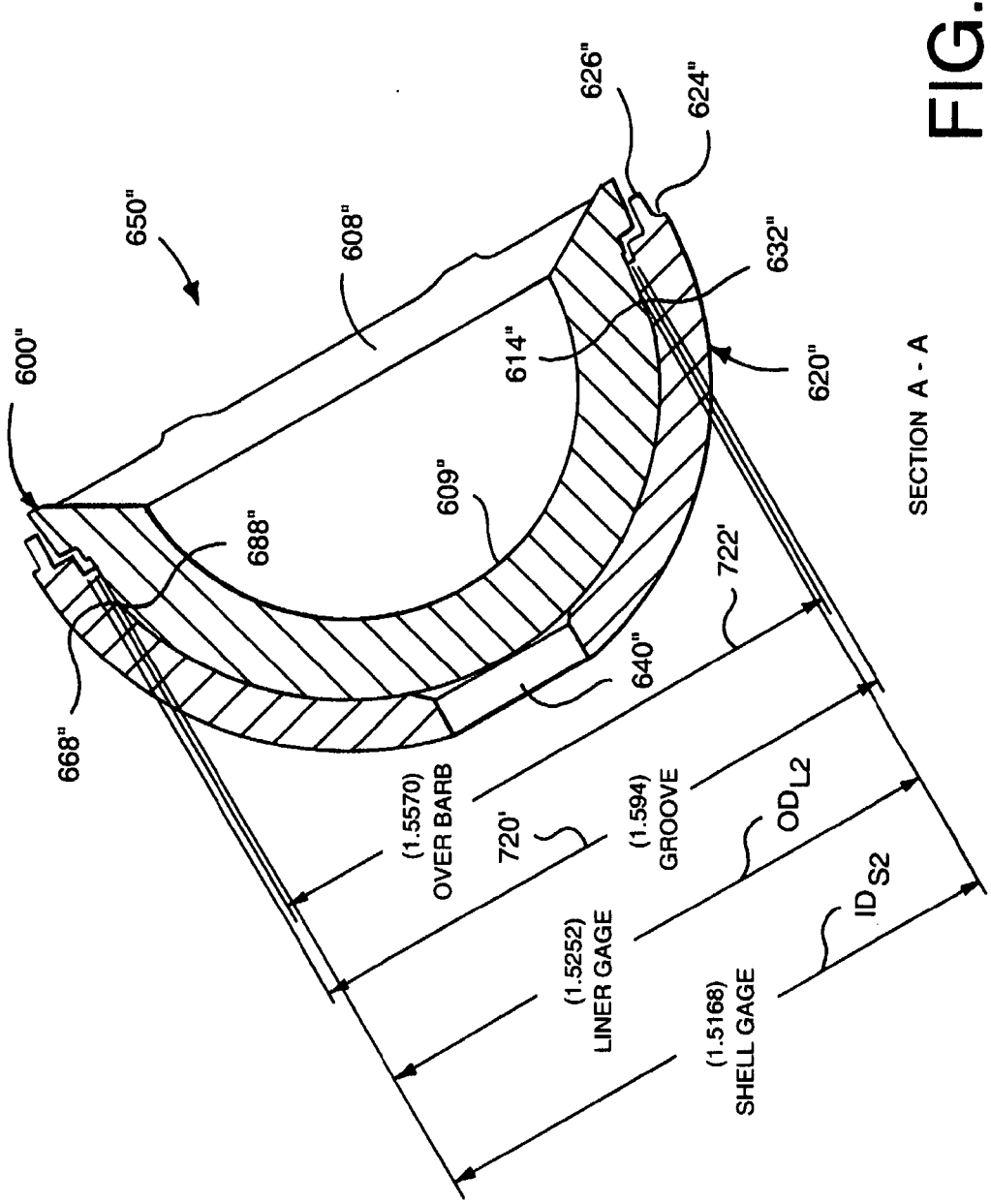
FIG. 39 is a sectional view of the prosthetic component assembly of FIG. 38 taken along line 39A-39A of FIG. 38.

As best depicted in FIG. 39, the LMC prosthetic component assembly 650" is such that when assembled, the inner diameter at the shell gage $ID_{S2}$ is slightly smaller than the outer diameter at the liner gage $OD_{L2}$. A groove diameter 720' of the shell 620" has a larger diameter than a barb diameter 722' of the liner 600".

Figure 40:
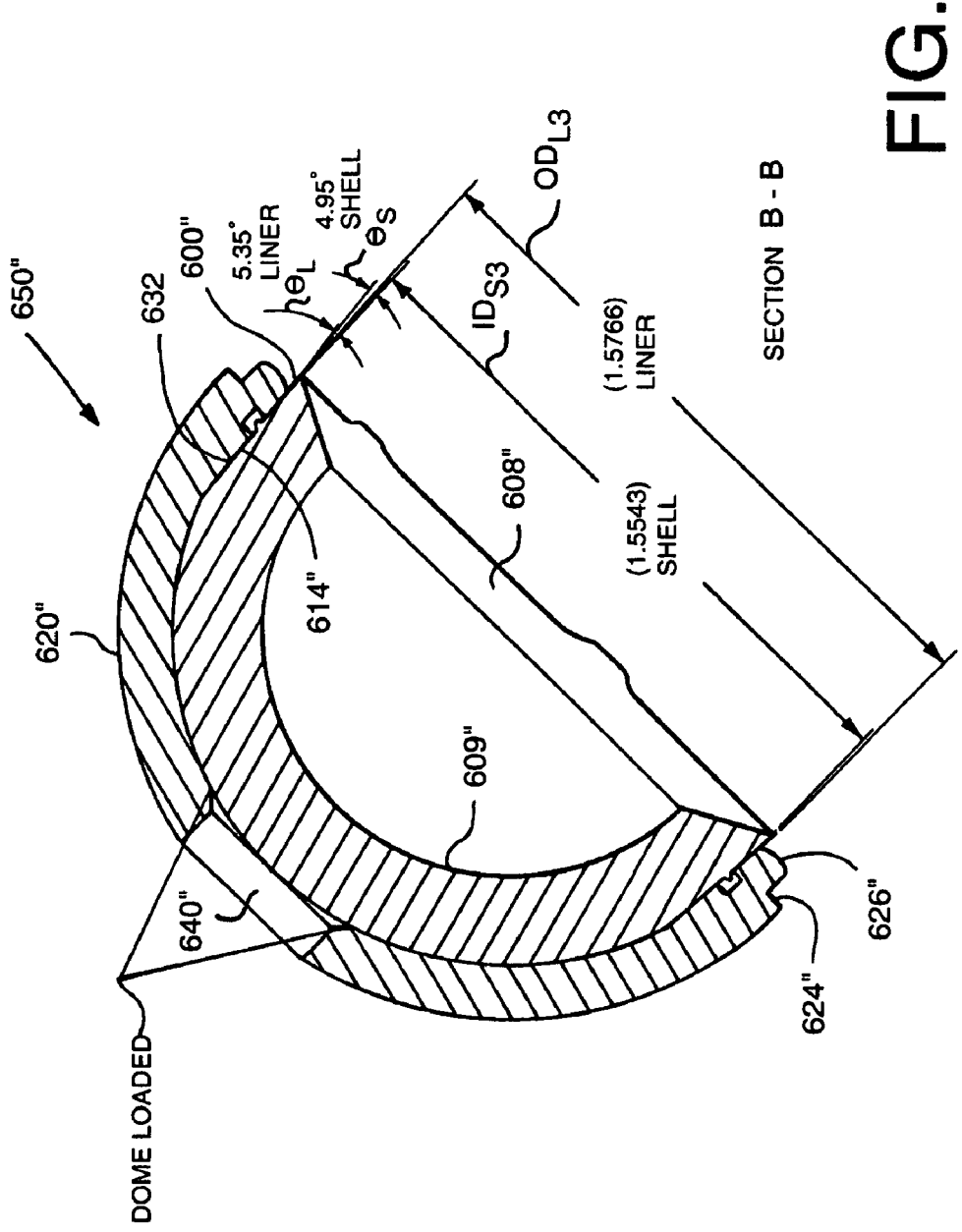
FIG. 40 is a sectional view of the prosthetic component assembly of FIG. 38 taken along line 40B-40B of FIG. 38.

As best depicted in FIG. 40, the angle $\theta_L$ of the liner (here at 5.35°) is greater than the angle $\theta_S$ of the shell (here at 4.95°). This creates an interference fit when assembled between the tapers 614" and 632". Pre-assembly, the liner 600" has a greater outer diameter ($OD_{L3}$) than the inner diameter ($ID_{S3}$) of the shell 620".

Figure 41:
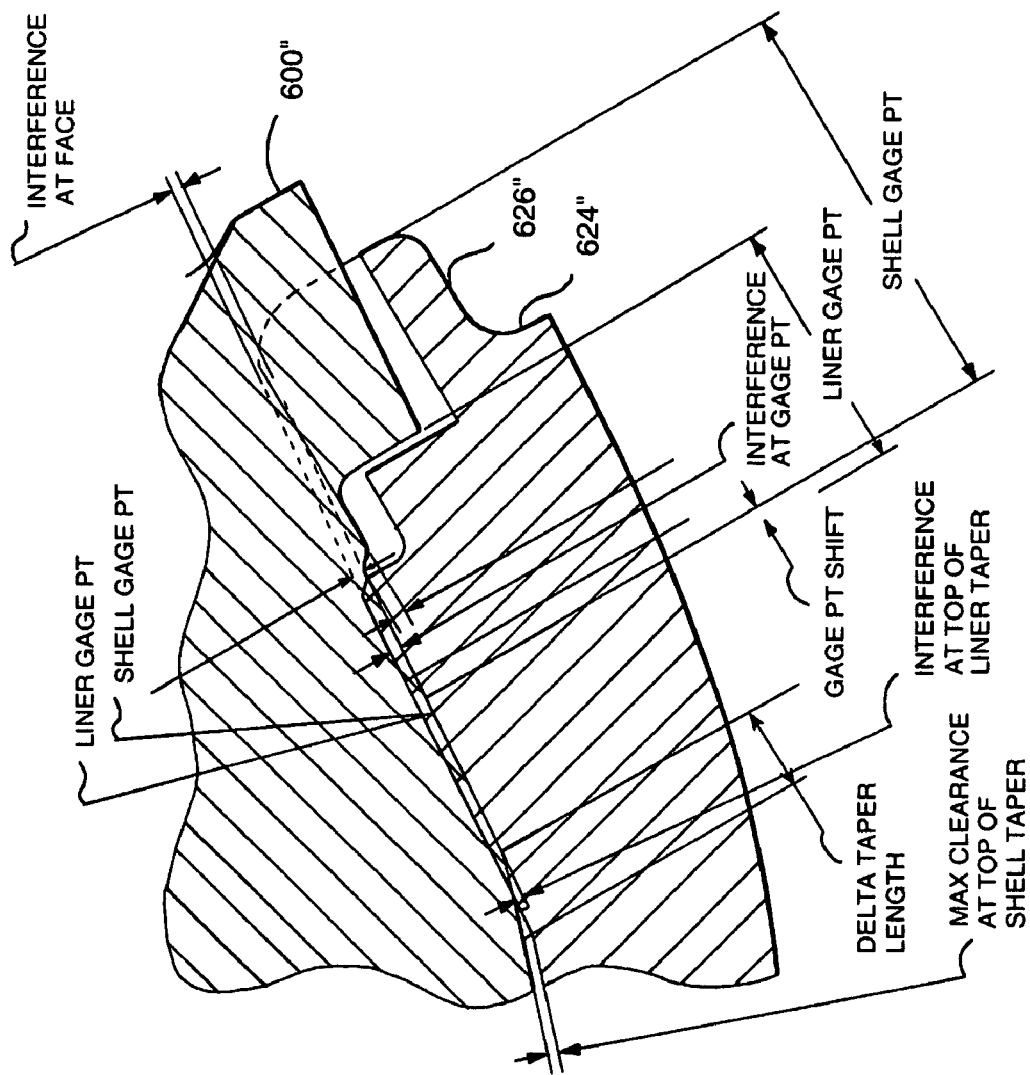
FIG. 41 is an enlarged, partial sectional view of a portion of the prosthetic component assembly of FIGS. 39 and 40 particularly illustrating the least material condition interference fit of the bearing insert and shell in accordance with the principles of the subject invention.

Such an interference fit is illustrated in FIG. 41. The interference at the liner face is projected beyond the liner 600" for illustrative purposes. Additionally shown in FIG. 42 is the congruity between the spherical radii of the liner 600" and the shell 620", the collinear gage points, the interference between the liner and shell at the gage points, the clearance at the dome end of the taper, the position of the liner and shell gage points, and other points.

Figure 42:
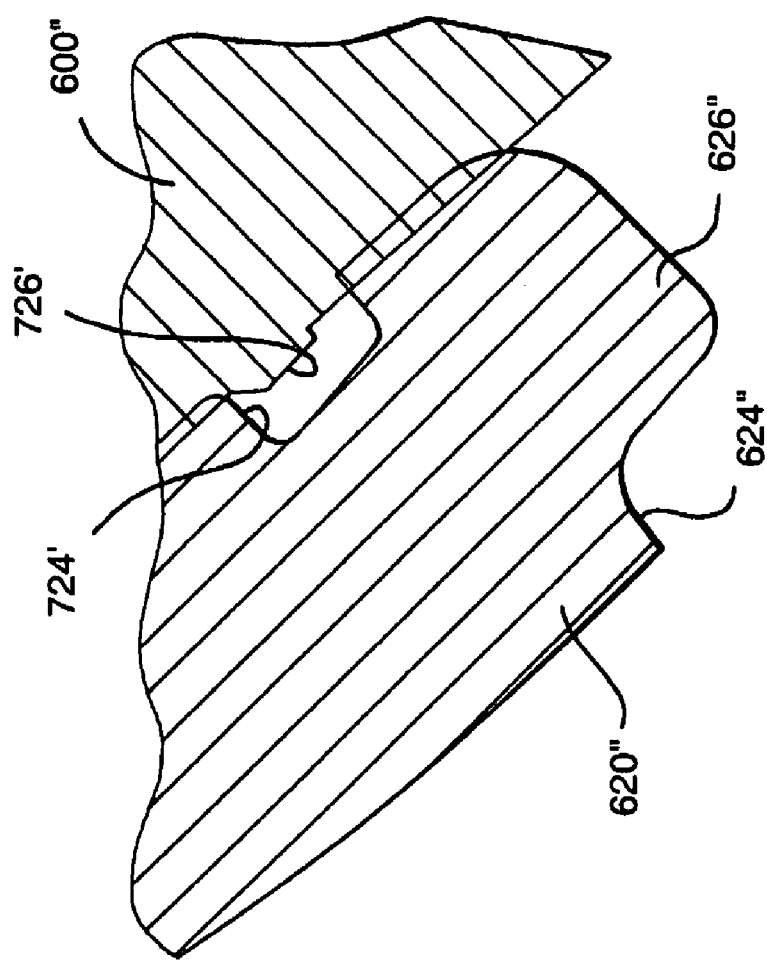
FIG. 42 is an enlarged, partial sectional view of a portion of the prosthetic component assembly of FIGS. 39 and 40 particularly illustrating positioning of a barb of the bearing insert in relation to a channel of the shell.

In FIG. 42, there is illustrated the channel or groove 724' on the inner surface of the shell 620". The liner 600" may include a barb 726' that is positioned in the channel 724' when the liner 600" is assembled into the shell 620".

Figure 22:
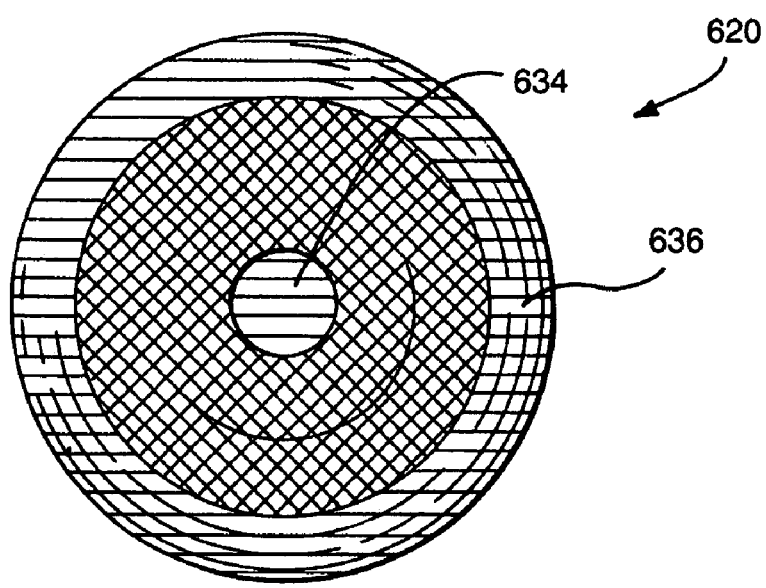
FIG. 22 is a top plan view of an embodiment of an acetabular cup assembly in accordance with the principles of the subject invention illustrating a loading pattern thereon.
Figure 23:
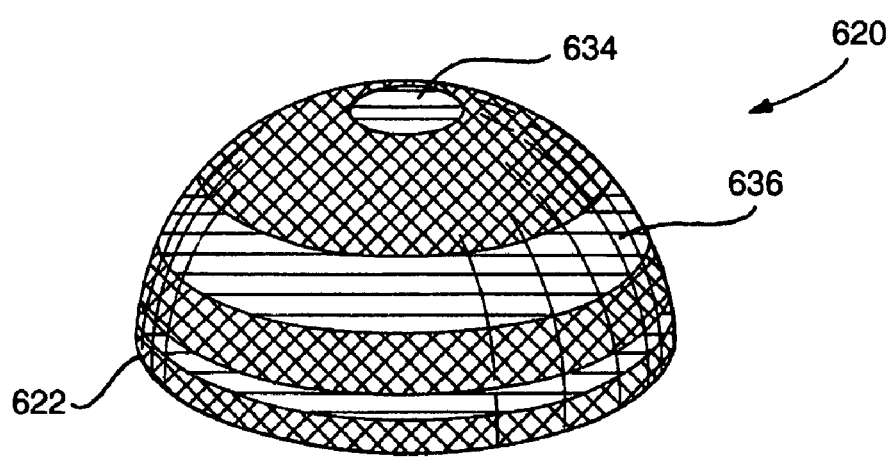
FIG. 23 is a perspective view of the acetabular cup assembly of FIG. 22 illustrating a loading pattern thereon.

Referring now to FIGS. 22 and 23, a loading pattern is shown for the prosthetic component assembly, generally designated 620 herein, defined by the components of FIGS. 24-42. The portion of the prosthetic component assembly 620 that is shaded depicts or represents congruency between the liner 600 and the shell 620 when a load is applied to the inside of the liner at 20° relative to an axis defined from the center opening 634. The shaded portion of the shell 636 may thus be considered a load pattern. Thus, the remaining portion of the shell 636 that is not shaded represents non-congruency between the liner and the shell.

Although the invention has been described in detail with reference to certain preferred embodiments, variations and modifications exist within the scope and spirit of the invention as described and defined in the following claims. For example, while the prosthetic cup assembly is disclosed in the context of a hip prosthesis, it has utility in other locations within a patient's body. Also, while the tapers of the various embodiments depicted in the drawings are shown to each be a straight taper, it should be understood that such tapers may assume other configurations such as a curve of a conic section—circle, ellipse, parabola, hyperbola or the like. However, if any such taper takes on a configuration that is non-straight, it should be appreciated that the respective mating taper should take on a complimentary configuration.

What is claimed is:

1. A prosthetic cup assembly defining a central axis, comprising:
   a shell configured to possess (i) a first frusto-conical inner surface that defines a first inner taper angle with respect to said central axis, and (ii) a second frusto-conical inner surface that defines a second inner taper angle with respect to said central axis; and
   a liner configured to possess (i) a first frusto-conical outer surface that defines a first outer taper angle with respect to said central axis, and (ii) a second frusto-conical outer surface that defines a second outer taper angle with respect to said central axis, said first frusto-conical outer surface and said second frusto-conical outer surface being positioned contiguous with respect to each other,
   wherein said first outer taper angle is equal to said first inner taper angle in a pre-assembly state of said liner,
   wherein said second outer taper angle is greater than said second inner taper angle in said pre-assembly state of said liner, and
   wherein in an assembled state both (i) said first frusto-conical outer surface engages said first frusto-conical inner surface, and (ii) said second frusto-conical outer surface engages said second frusto-conical inner surface to couple said liner to said shell.

2. The prosthetic cup assembly of claim 1, wherein:
   0°<said first inner taper angle≦22.5°,
   0°<said second inner taper angle≦22.5°,
   0°<said first outer taper angle≦22.5°, and
   0°<said second outer taper angle≦22.5°.

3. The prosthetic cup assembly of claim 1, wherein:
   said first frusto-conical outer surface possesses a first vertical height VH1,
   said second frusto-conical outer surface possesses a second vertical height VH2, and
   2VH1=VH2.

4. The prosthetic cup assembly of claim 1, wherein said liner is formed of polyethylene and said shell is formed of metal.

5. The prosthetic cup assembly of claim 4, wherein said metal comprises one of titanium and cobalt chromium.

6. The prosthetic cup assembly of claim 1, wherein:
   said shell defines a cavity, and
   said liner is received within said cavity when said prosthetic cup assembly is in an assembled state.

7. The prosthetic cup assembly of claim 6, wherein said liner is spaced apart from said shell when said liner is in said pre-assembly state.

8. The prosthetic cup assembly of claim 1, wherein:
   said first inner taper angle is equal to said second inner taper angle.

9. A prosthetic cup assembly defining a central axis, comprising:
   a shell configured to possess (i) a first frusto-conical inner surface that defines a first inner taper angle with respect to said central axis, and (ii) a second frusto-conical inner surface that defines a second inner taper angle with respect to said central axis; and
   a liner configured to possess (i) a first frusto-conical outer surface that defines a first outer taper angle with respect to said central axis, and (ii) a second frusto-conical outer surface that defines a second outer taper angle with respect to said central axis, said first frusto-conical outer surface and said second frusto-conical outer surface being positioned contiguous with respect to each other,
   wherein said first outer taper angle is less than or equal to said first inner taper angle in a pre-assembly state of said liner,
   wherein said second outer taper angle is greater than said second inner taper angle in said pre-assembly state of said liner, and
   wherein in an assembled state both (i) said first frusto-conical outer surface engages said first frusto-conical inner surface, and (ii) said second frusto-conical outer surface engages said second frusto-conical inner surface to couple said liner to said shell.

10. The prosthetic cup assembly of claim 9, wherein:
    0°<said first inner taper angle≦22.5°,
    0°<said second inner taper angle≦22.5°,
    0°<said first outer taper angle≦22.5°, and
    0°<said second outer taper angle≦22.5°.

11. The prosthetic cup assembly of claim 9, wherein:
    said first frusto-conical outer surface possesses a first vertical height VH1,
    said second frusto-conical outer surface possesses a second vertical height VH2, and
    2VH1=VH2.

12. The prosthetic cup assembly of claim 9, wherein said liner is formed of polyethylene and said shell is formed of metal.

13. The prosthetic cup assembly of claim 12, wherein said metal comprises one of titanium and cobalt chromium.

14. The prosthetic cup assembly of claim 9, wherein:
said shell defines a cavity, and
said liner is received within said cavity when said prosthetic cup assembly is in an assembled state.

15. The prosthetic cup assembly of claim 14, wherein said liner is spaced apart from said shell when said liner is in said pre-assembly state.

16. The prosthetic cup assembly of claim 9, wherein:
said first inner taper angle is equal to said second inner taper angle.

17. A method of assembling a prosthetic cup assembly that defines a central axis, comprising:
providing a shell having (i) a first frusto-conical inner surface that defines a first inner taper angle with respect to said central axis, and (ii) a second frusto-conical inner surface that defines a second inner taper angle with respect to said central axis;
providing a liner having (i) a first frusto-conical outer surface that defines a first outer taper angle with respect to said central axis, and (ii) a second frusto-conical outer surface that defines a second outer taper angle with respect to said central axis, said first frusto-conical outer surface and said second frusto-conical outer surface being positioned contiguous with respect to each other, and said first outer taper angle being less than or equal to said first inner taper angle in a pre-assembly state of said liner, and further said second outer taper angle being greater than said second inner taper angle in said pre-assembly state of said liner; and
engaging both (i) said first frusto-conical outer surface with said first frusto-conical inner surface, and (ii) said second frusto-conical outer surface with said second frusto-conical inner surface so as to couple said liner to said shell.

18. The method of claim 17, wherein:
$0° <$ said first inner taper angle $\leq 22.5°$,
$0° <$ said second inner taper angle $\leq 22.5°$,
$0° <$ said first outer taper angle $\leq 22.5°$, and
$0° <$ said second outer taper angle $\leq 22.5°$.

19. The method of claim 17, wherein:
said first frusto-conical outer surface possesses a first vertical height VH1,
said second frusto-conical outer surface possesses a second vertical height VH2, and
2VH1=VH2.

20. The method of claim 17, wherein said liner is formed of polyethylene and said shell is formed of metal.

21. The method of claim 20, wherein said metal comprises one of titanium and cobalt chromium.

22. The method of claim 17, wherein:
said prosthetic cup assembly is in an assembled state after said engaging step, and
said liner is in said pre-assembly state prior to said engaging step.

23. The method of claim 17, wherein:
said first inner taper angle is equal to said second inner taper angle.

* * * * *

UNITED STATES PATENT AND TRADEMARK OFFICE
CERTIFICATE OF CORRECTION

PATENT NO.        : 7,326,253 B2                                            Page 1 of 1
APPLICATION NO. : 10/278577
DATED             : February 5, 2008
INVENTOR(S)       : Snyder et al.

It is certified that error appears in the above-identified patent and that said Letters Patent is hereby corrected as shown below:

Title page, item (12) under UNITED STATES PATENT should read as following:
    Snyder et al.

Title page, item (75) should read as following:
    Inventors: Duane G. Snyder, Scottsdale, AZ (US);
              Leanne A. Turner, North Webster, IN (US);
              James G. Lancaster, Warsaw, IN (US);
              Paul P. Lewis, Warsaw, IN (US)

Signed and Sealed this

Twenty-second Day of July, 2008

JON W. DUDAS
*Director of the United States Patent and Trademark Office*